(12) United States Patent
Gui et al.

(10) Patent No.: US 11,852,618 B2
(45) Date of Patent: *Dec. 26, 2023

(54) DETECTING INFECTION OF PLANT DISEASES BY CLASSIFYING PLANT PHOTOS

(71) Applicant: CLIMATE LLC, Saint Louis, MO (US)

(72) Inventors: Yichuan Gui, Pacifica, CA (US); Wei Guan, Pleasanton, CA (US)

(73) Assignee: CLIMATE LLC, Saint Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/003,914

(22) Filed: Aug. 26, 2020

(65) Prior Publication Data
US 2020/0393435 A1 Dec. 17, 2020

Related U.S. Application Data

(63) Continuation of application No. 16/658,021, filed on Oct. 18, 2019, now Pat. No. 10,761,075.
(Continued)

(51) Int. Cl.
*G06N 3/08* (2023.01)
*G06K 9/62* (2022.01)
(Continued)

(52) U.S. Cl.
CPC ......... *G01N 33/0098* (2013.01); *G06F 18/23* (2023.01); *G06F 18/2431* (2023.01);
(Continued)

(58) Field of Classification Search
CPC .. G01N 33/0098; G01N 33/12; G06K 9/6217; G06K 9/6218; G06K 9/6219;
(Continued)

(56) References Cited

U.S. PATENT DOCUMENTS

| 5,841,883 A | 11/1998 | Kono |
| 8,712,148 B2 | 4/2014 | Paris et al. |
| (Continued) | | |

FOREIGN PATENT DOCUMENTS

| CN | 103778428 | 5/2014 |
| CN | 106599939 | 4/2017 |
| (Continued) | | |

OTHER PUBLICATIONS

N. Petrellis, "A smart phone image processing application for plant disease diagnosis," 2017 6th International Conference on Modern Circuits and Systems Technologies (MOCAST), 2017, pp. 1-4, doi: 10.1109/MOCAST.2017.7937683. (Year: 2017).*
(Continued)

*Primary Examiner* — Vikkram Bali
(74) *Attorney, Agent, or Firm* — Harness, Dickey & Pierce, P.L.C.

(57) ABSTRACT

A system and processing methods for configuring and utilizing a convolutional neural network (CNN) for plant disease recognition are disclosed. In some embodiments, the system is programmed to collect photos of infected plants or leaves where regions showing symptoms of infecting diseases are marked. Each photo may have multiple marked regions. Depending on how the symptoms are sized or clustered, one marked region may include only one lesion caused by one disease, while another may include multiple, closely-spaced lesions caused by one disease. The system is programmed to determine anchor boxes having distinct aspect ratios from these marked regions for each convolutional layer of a single shot multibox detector (SSD). For certain types of plants, common diseases lead to relatively many aspect ratios, some having relatively extreme values. The system is programmed to then train the SSD using the
(Continued)

marked regions and the anchor boxes and apply the SSD to new photos to identify diseased plants.

16 Claims, 10 Drawing Sheets

Related U.S. Application Data

(60) Provisional application No. 62/748,288, filed on Oct. 19, 2018.

(51) Int. Cl.
*G01N 33/00* (2006.01)
*G06F 18/23* (2023.01)
*G06F 18/2431* (2023.01)
*G06V 10/764* (2022.01)
*G06V 10/82* (2022.01)
*G06V 20/10* (2022.01)
*G06V 20/00* (2022.01)

(52) U.S. Cl.
CPC .............. *G06N 3/08* (2013.01); *G06V 10/764* (2022.01); *G06V 10/82* (2022.01); *G06V 20/188* (2022.01); *G06V 20/38* (2022.01)

(58) Field of Classification Search
CPC .... G06K 9/628; G06K 9/6281; G06K 9/6282; G06K 9/6284; G06V 10/82; G06V 10/70; G06V 20/188; G06V 20/194; G06V 20/10; G06V 20/38; G06V 20/40
USPC .......................... 382/110, 100, 103, 128, 209
See application file for complete search history.

(56) References Cited

U.S. PATENT DOCUMENTS

| | | | |
|---|---|---|---|
| 8,738,243 | B2 | 5/2014 | Sauder et al. |
| 8,767,194 | B2 | 7/2014 | Preiner et al. |
| 10,761,075 | B2 | 9/2020 | Gui et al. |
| 10,768,340 | B2 | 9/2020 | Koch et al. |
| 2013/0136312 | A1 | 5/2013 | Tseng |
| 2015/0094916 | A1 | 4/2015 | Bauerer et al. |
| 2016/0050840 | A1 | 2/2016 | Sauder et al. |
| 2016/0216245 | A1 | 7/2016 | Sutton |
| 2018/0276845 | A1* | 9/2018 | Bjorgvinsdottir ......... G06T 7/73 |
| 2019/0108413 | A1 | 4/2019 | Chen |
| 2019/0304102 | A1* | 10/2019 | Chen ........................ G06T 7/11 |
| 2020/0124581 | A1 | 4/2020 | Gui |

FOREIGN PATENT DOCUMENTS

| | | |
|---|---|---|
| CN | 108541683 | 9/2018 |
| CN | 108596017 | 9/2018 |
| KR | 2018/00523003 A | 5/2018 |
| WO | WO 2013/149038 A1 | 10/2013 |
| WO | WO 2016/029054 A1 | 2/2016 |
| WO | WO2016/176355 | 11/2016 |

OTHER PUBLICATIONS

Li, Y., Luo, Z., Wang, F., & Wang, Y. (2020). Hyperspectral Leaf Image-Based Cucumber Disease Recognition Using the Extended Collaborative Representation Model. Sensors (Basel, Switzerland), 20(14), 4045. https://doi.org/10.3390/s20144045 (Year: 2020).*

Kabir, Muhammad Mohsin, Abu Quwsar Ohi and M. Mridha. "A Multi-Plant Disease Diagnosis Method using Convolutional Neural Network." ArXiv abs/2011.05151 (2020): n. pag. (Year: 2020).*

Liu, W., Dragomir Anguelov, D. Erhan, Christian Szegedy, Scott E. Reed, Cheng-Yang Fu and Alexander C. Berg. "SSD: Single Shot MultiBox Detector." ECCV (2016). (Year: 2016).*

Fuentes A, Yoon S, Kim SC, Park DS. A Robust Deep-Learning-Based Detector for Real-Time Tomato Plant Diseases and Pests Recognition. Sensors (Basel). Sep. 4, 2017;17(9):2022. doi: 10.3390/s17092022. PMID: 28869539; PMCID: PMC5620500. (Year: 2017).*

The International Searching Authority, "Search Report" in application No. PCT/US19/57066, dated Jan. 9, 2020, 13 pages.

Liu et al., "SSD: Single Shot MultiBox Detector", Computer Vision and Pattern Recognition, dated Dec. 29, 2016, 17 pages.

Current Claims in application No. PCT/US19/57066, dated Jan. 2020, 5 pages.

Gui, U.S. Appl. No. 16/658,021, filed Oct. 18, 2019, Office Action, dated Apr. 27, 2020.

Gui, U.S. Appl. No. 16/658,021, filed Oct. 18, 2019, Notice of Allowance, dated Jul. 17, 2020.

Ferentinos Konstantinos P: "Deep learning models for plant disease detection and diagnosis", Computers and electronics in Agriculture, Elsevier, Amsterdam, NL, vol. 145, Feb. 5, 2018 (Feb. 5, 2018), pp. 311-318.

* cited by examiner

Fig. 2
(a)
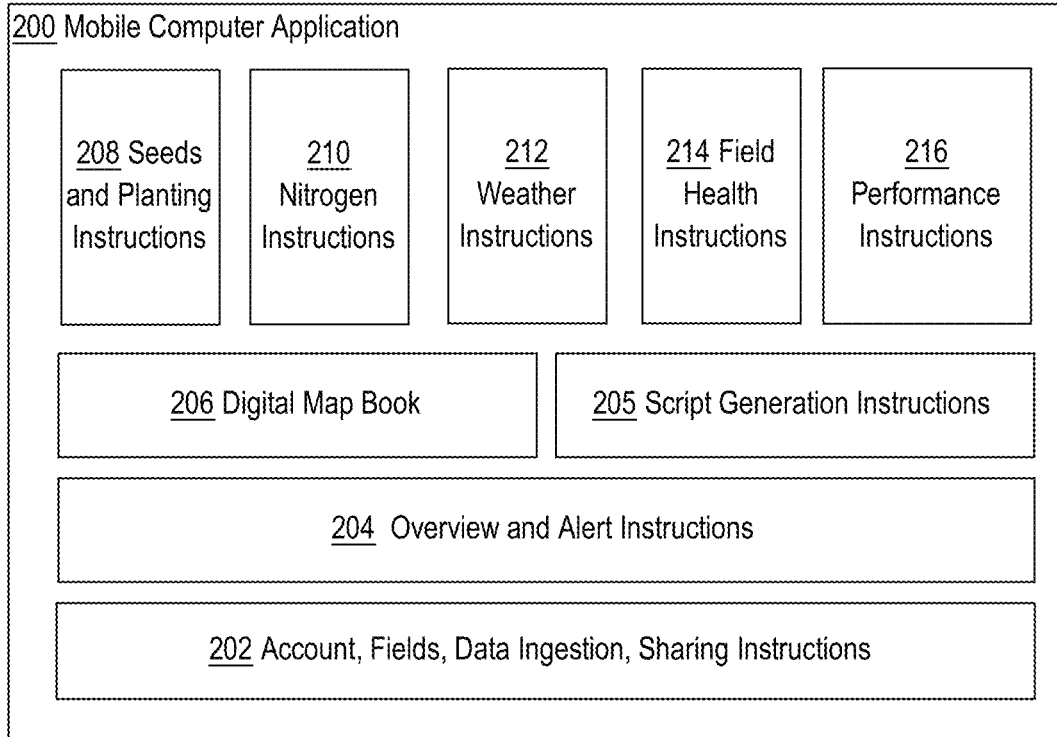
(b)
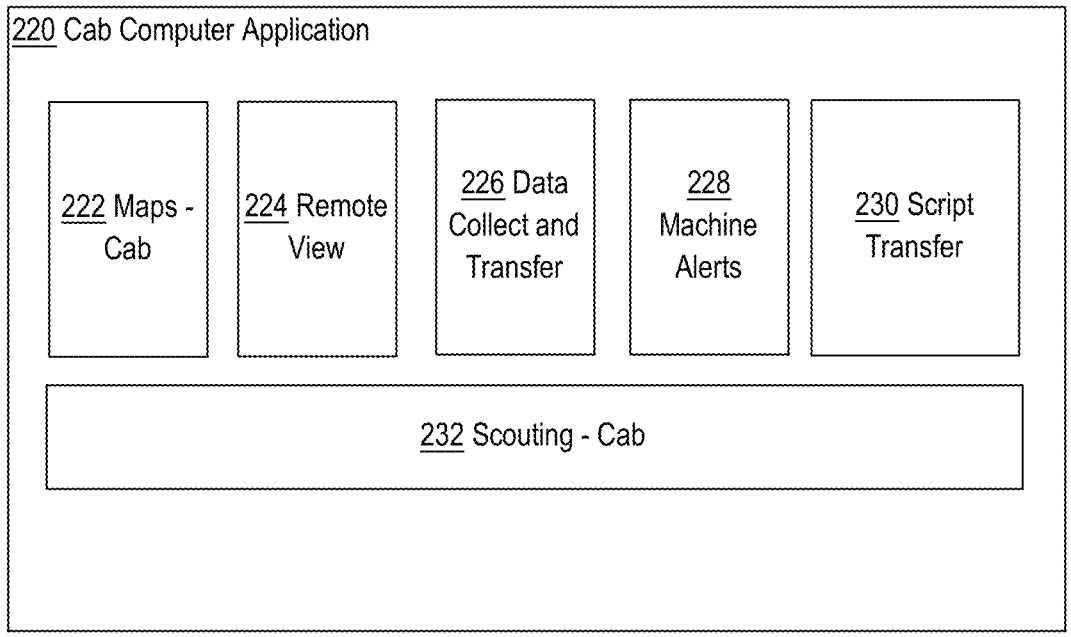

FIG. 5

Data Manager

Nitrogen | Planting | Practices | Soil

Planting 1 (4 Fields)
Crop Corn Product
Plant Date: 2016-04-12
ILU 112 | Pop: 34000
[Edit] [Apply]

Planting 2 (0 Fields)
Crop Corn Product
Plant Date: 2016-04-15
ILU 83 | Pop: 34000
[Edit] [Apply]

Planting 3 (0 Fields)
Crop Corn Product
Plant Date: 2016-04-13
ILU 83 | Pop: 34000
[Edit] [Apply]

Planting 4 (1 Fields)
Crop Corn Product
Plant Date: 2016-04-13
ILU 112 | Pop: 34000
[Edit] [Apply]

[+ Add New Planting Plan]

| | CROP | PLANTED ACRES | PRODUCT | RELATIVE MATURITY | TARGET YIELD | POPULATION (AVG) | PLA |
|---|---|---|---|---|---|---|---|
| ☐ Select All | | | | | | | |
| ☐ Ames, IA 1<br>Corn \| 100 \| Boone, IA | Corn | — | DMC82-M | 112 | 160 | 34000 | Apr |
| ☑ Austin, MN 1<br>Corn \| 100 \| Fredricks, MN | Corn | — | DMC82-M | 114 | 160 | 36000 | Apr |
| ☐ Boone, IN 1<br>Corn \| 100 \| Boone, IA | Corn | — | DMC82-M | 112 | 150 | 34000 | Apr |
| ☐ Champaign 1<br>Corn \| 100 \| Champaign, IL | Corn | — | — | 112 | 200 | 34000 | Apr |
| ☐ E Nebraska 1<br>Corn \| 100 \| Burt, NE | Corn | — | — | 112 | 160 | 34000 | Apr |

*FIG. 6*

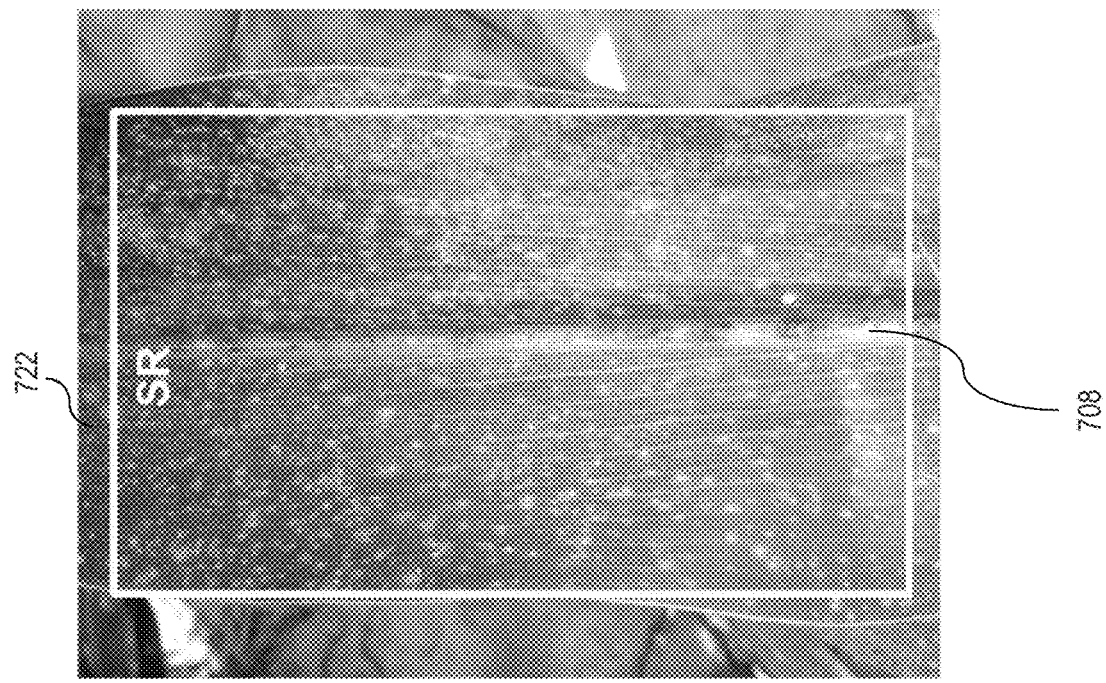
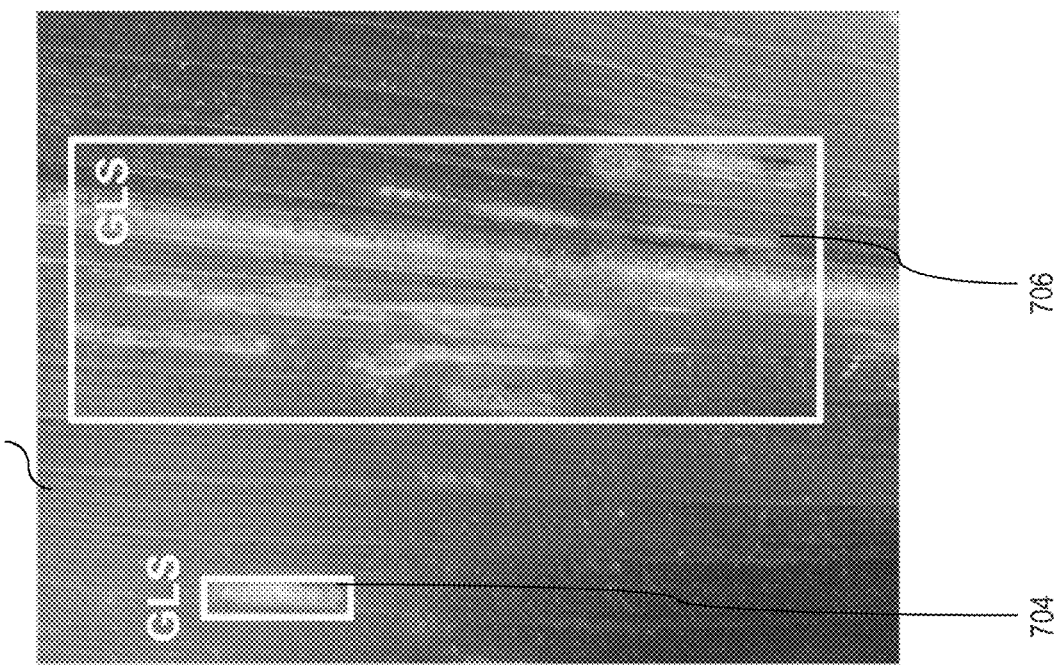
Fig. 7A

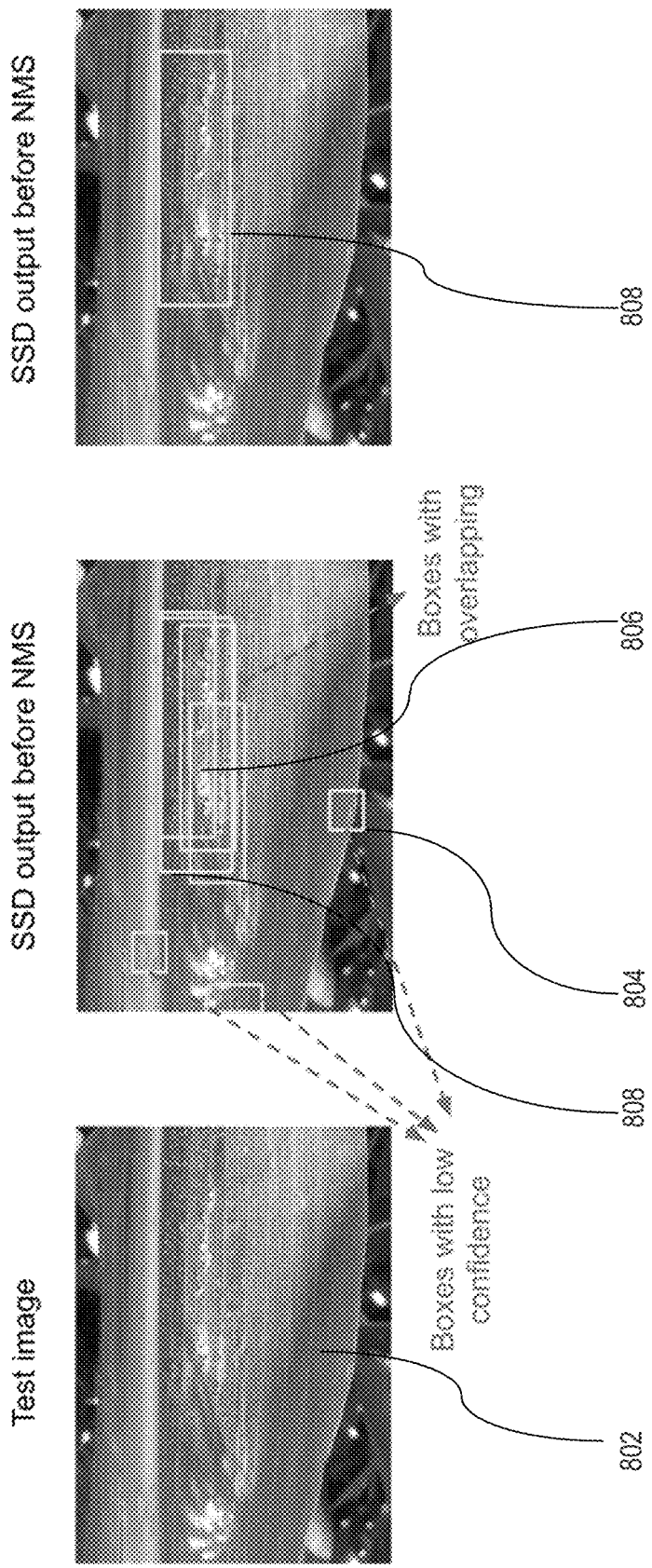

Fig. 9

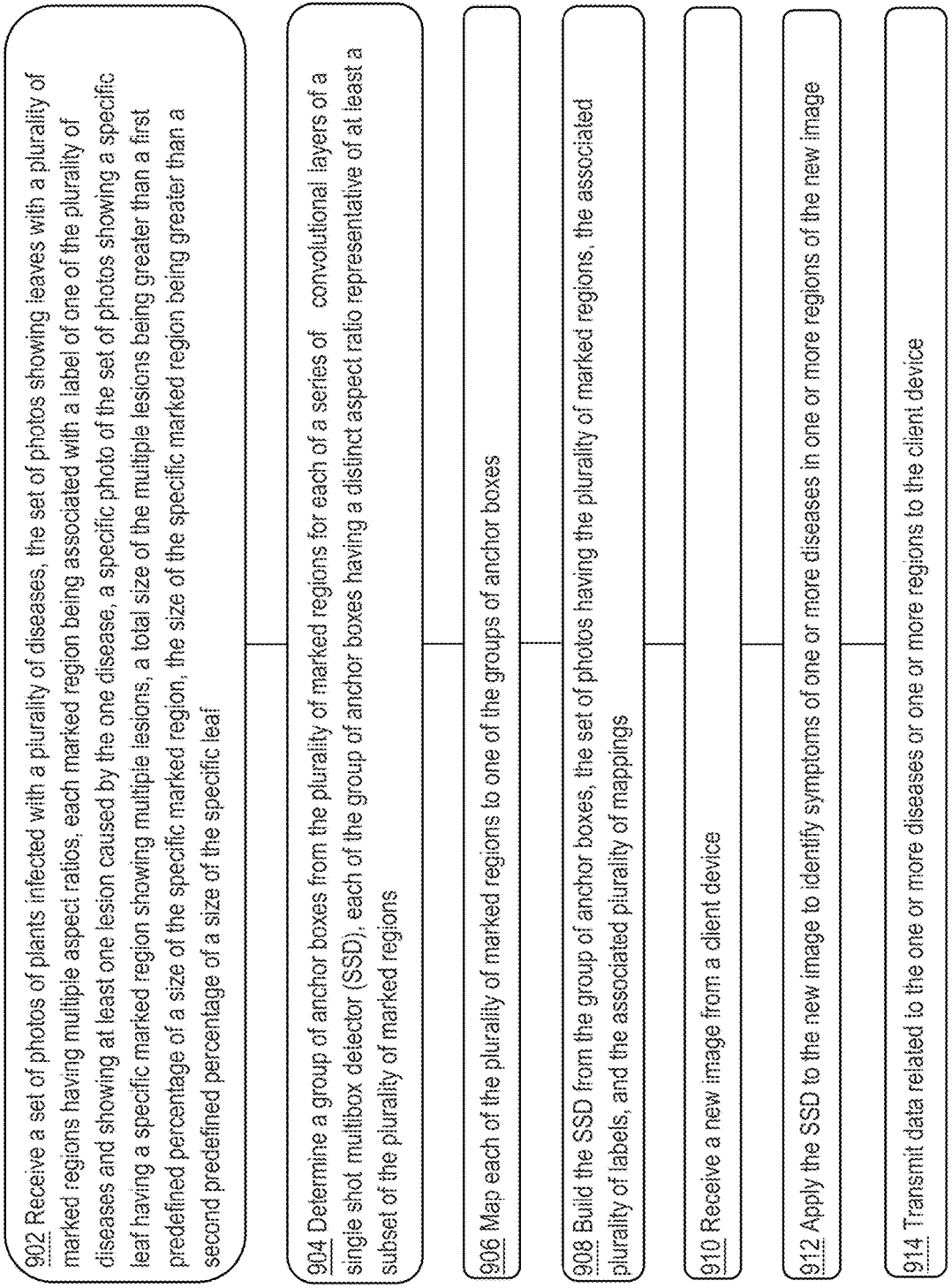

902 Receive a set of photos of plants infected with a plurality of diseases, the set of photos showing leaves with a plurality of marked regions having multiple aspect ratios, each marked region being associated with a label of one of the plurality of diseases and showing at least one lesion caused by the one disease, a specific photo of the set of photos showing a specific leaf having a specific marked region showing multiple lesions, a total size of the multiple lesions being greater than a first predefined percentage of a size of the specific marked region, the size of the specific marked region being greater than a second predefined percentage of a size of the specific leaf 904 Determine a group of anchor boxes from the plurality of marked regions for each of a series of convolutional layers of a single shot multibox detector (SSD), each of the group of anchor boxes having a distinct aspect ratio representative of at least a subset of the plurality of marked regions 906 Map each of the plurality of marked regions to one of the groups of anchor boxes 908 Build the SSD from the group of anchor boxes, the set of photos having the plurality of marked regions, the associated plurality of labels, and the associated plurality of mappings 910 Receive a new image from a client device 912 Apply the SSD to the new image to identify symptoms of one or more diseases in one or more regions of the new image 914 Transmit data related to the one or more diseases or one or more regions to the client device

DETECTING INFECTION OF PLANT DISEASES BY CLASSIFYING PLANT PHOTOS

BENEFIT CLAIM

This application claims the benefit under 35 U.S.C. § 120 as a Continuation of application Ser. No. 16/658,021, filed Oct. 18, 2019, which claims the benefit under 35 U.S. C. § 119(e) of provisional application 62/748,288, filed Oct. 19, 2018, the entire contents of which are hereby incorporated by reference for all purposes as if fully set forth herein. Applicant hereby rescinds any disclaimer of claim scope in the parent applications or the prosecution history thereof and advises the USPTO that the claims in this application may be broader than any claim in the parent applications.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright or rights whatsoever. © 2015-2020 The Climate Corporation.

FIELD OF THE DISCLOSURE

The present disclosure relates to the technical areas of plant disease detection and machine learning. The present disclosure also relates to the technical area of improving configuration and training of machine learning models for plant disease recognition.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Plant disease detection is important in agriculture. Today an automated approach often involves classifying plant photos, which can be implemented by applying a convolutional neural network (CNN) having a plurality of convolutional layers. Some CNNs work together in a two-stage approach, where the first CNN is used to propose regions of interest within given images and a second CNN is then used to classify each proposed region. Some CNNs require all images to be of a fixed size. There are CNNs that can take images of various sizes and propose and classify regions of interest in one shot with superior performance. Given the distinct symptoms of plant diseases, it would be helpful to specifically configure and train such a CNN to classify plant photos and detect infection of plant diseases to promote plant health and growth.

SUMMARY

The appended claims may serve as a summary of the disclosure.

BRIEF DESCRIPTION OF THE DRAWINGS

In the drawings:

FIG. 2 illustrates two views of an example logical organization of sets of instructions in main memory when an example mobile application is loaded for execution.

FIG. 5 depicts an example embodiment of a timeline view for data entry.

FIG. 6 depicts an example embodiment of a spreadsheet view for data entry.

FIG. 7A includes example photos of corn leaves each having symptoms of one disease.

FIG. 8 illustrates an example process of applying non-maximum suppression to refine an initial classification result to a final classification result.

FIG. 9 illustrates an example method performed by a server computer that is programmed for configuring and utilizing a convolutional neural network for plant disease detection.

DETAILED DESCRIPTION

Figure 1:
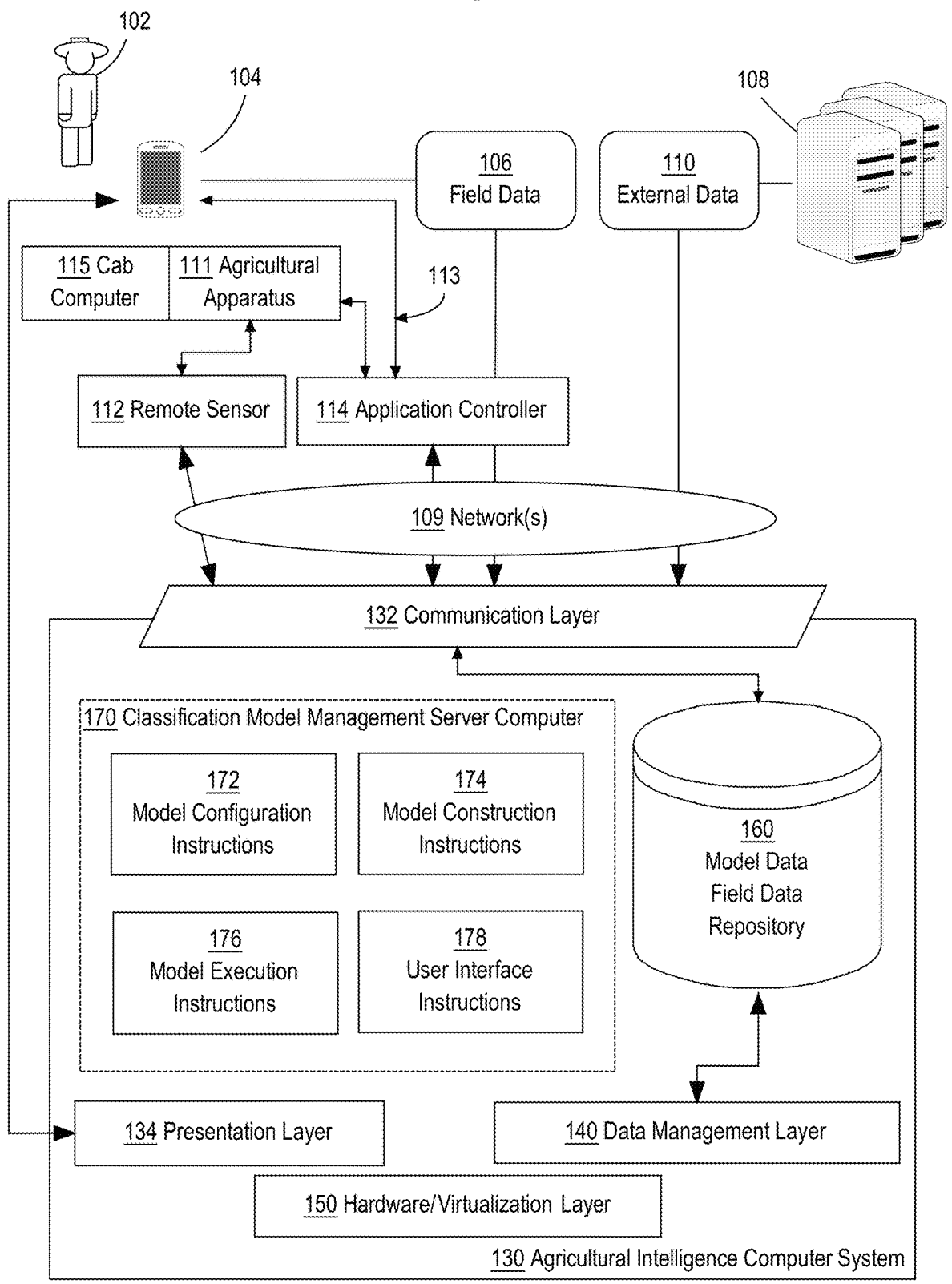
FIG. 1 illustrates an example computer system that is configured to perform the functions described herein, shown in a field environment with other apparatus with which the system may interoperate.

In the following description, for the purposes of explanation, numerous specific details are set forth in order to provide a thorough understanding of the present disclosure. It will be apparent, however, that embodiments may be practiced without these specific details. In other instances, well-known structures and devices are shown in block diagram form in order to avoid unnecessarily obscuring the present disclosure. Embodiments are disclosed in sections according to the following outline:

1. GENERAL OVERVIEW
2. EXAMPLE AGRICULTURAL INTELLIGENCE COMPUTER SYSTEM
   2.1. STRUCTURAL OVERVIEW
   2.2. APPLICATION PROGRAM OVERVIEW
   2.3. DATA INGEST TO THE COMPUTER SYSTEM
   2.4. PROCESS OVERVIEW—AGRONOMIC MODEL TRAINING
   2.5. IMPLEMENTATION EXAMPLE—HARDWARE OVERVIEW
3. FUNCTIONAL DESCRIPTIONS
   3.1 PLANT DISEASE DETECTION
   3.2 DIGITAL MODEL CONFIGURATION
   3.3 TRAINING SET AND DIGITAL MODEL CONSTRUCTION
   3.4 DIGITAL MODEL EXECUTION
   3.5 EXAMPLE PROCESSES
4. EXTENSIONS AND ALTERNATIVES

1. General Overview

A system and processing methods for configuring and utilizing a convolutional neural network (CNN) for plant disease recognition are disclosed. In some embodiments, the system is programmed to collect photos of infected plants or leaves where regions showing symptoms of infecting diseases are marked. Each photo may have multiple marked regions. Depending on how the symptoms are sized or clustered, one marked region may include only one lesion caused by one disease, while another may include multiple, closely-spaced lesions caused by one disease. The system is programmed to determine anchor boxes (default boxes) having distinct aspect ratios from these marked regions for each convolutional layer of a single shot multibox detector (SSD). For certain types of plants, common diseases lead to relatively many aspect ratios, some having relatively extreme values. The system is programmed to then train the SSD using the marked regions and the anchor boxes and apply the SSD to new photos to identify diseased plants.

In some embodiments, the system is programmed to collect marked photos of corn leaves. Each photo may have one or more marked regions (ground truth boxes). Each marked region may have one or more lesions caused by one of a plurality of corn diseases and is labeled with the one corn disease. The system can be programmed to further process the marked regions. Specifically, the system can be programmed to break a marked region into several or combine several marked regions into one based on how regions corresponding to the lesions are sized or clustered in the photo. For example, an expert might have marked in a photo two portions of a big cluster of lesions caused by Southern Rust. The system can be programmed to merge and expand the two portions into one marked region covering the entire cluster because the regions corresponding to disconnected lesions in the cluster are spaced close together and the cluster covers up most of the leaf.

In some embodiments, the system is programmed to determine anchor boxes for each of a series of convolutional layers of an SSD from the resulting marked regions. See Liu W. et al. (2016) SSD: Single Shot MultiBox Detector. In: Leibe B., Matas J., Sebe N., Welling M. (eds) *Computer Vision—ECCV* 2016, pp 21-37. Lecture Notes in Computer Science, vol 9905. Springer, Cham. The system can be programmed to normalize and cluster the marked regions and compute an aggregate for each cluster for defining an anchor box. Each anchor box can thus have a distinct scale and aspect ratio, representative of a subset of the marked regions showing symptoms of a common corn disease. For some corn diseases, the aspect ratio can range from 1/7 to 7.

In some embodiments, the system is programmed to map each marked region to an anchor box based on the shape of the marked region. Specifically, the system can be configured to conclude a successful mapping when a superimposition of the anchor box can cover more than a predefined percentage of the marked region. The system is programmed to then train an SSD with images having the marked regions, the corresponding labels, the anchor boxes, and the mappings.

In some embodiments, the system is programmed to receive a new photo of a corn leaf from a client device and apply the SSD to the new photo to receive an initial identification of multiple regions in the photo and a classification into one of the corn diseases for each of the multiple regions with a corresponding confidence score. When the same region is classified into multiple corn diseases, some classifications associated with relatively low confidence scores can be filtered out. The system is programmed to then transmit the classification results to the client device.

The system produces various technical benefits. An SSD has been shown to achieve better performance than similar CNNs, being faster than previous single shot detectors and also more accurate, in fact as accurate as slower techniques that perform explicit region proposals and pooling. The system provides an approach for configuring and training an SSD that is especially suitable for classifying certain types of objects, such as plant disease symptoms. These symptoms comprise lesions that are sized and positioned in specific manners, and the approach provided by the system captures that specificity and thus further improves performance of the SSD in classifying plant disease symptoms. Such improvement in turn leads to better health and growth of crops.

Other aspects and features of embodiments will become apparent from other sections of the disclosure.

2. Example Agricultural Intelligence Computer System 2.1 Structural Overview

FIG. 1 illustrates an example computer system that is configured to perform the functions described herein, shown in a field environment with other apparatus with which the system may interoperate. In one embodiment, a user 102 owns, operates or possesses a field manager computing device 104 in a field location or associated with a field location such as a field intended for agricultural activities or a management location for one or more agricultural fields. The field manager computer device 104 is programmed or configured to provide field data 106 to an agricultural intelligence computer system 130 via one or more networks 109.

Examples of field data 106 include (a) identification data (for example, acreage, field name, field identifiers, geographic identifiers, boundary identifiers, crop identifiers, and any other suitable data that may be used to identify farm land, such as a common land unit (CLU), lot and block number, a parcel number, geographic coordinates and boundaries, Farm Serial Number (FSN), farm number, tract number, field number, section, township, and/or range), (b) harvest data (for example, crop type, crop variety, crop rotation, whether the crop is grown organically, harvest date, Actual Production History (APH), expected yield, yield, crop price, crop revenue, grain moisture, tillage practice, and previous growing season information), (c) soil data (for example, type, composition, pH, organic matter (OM), cation exchange capacity (CEC)), (d) planting data (for example, planting date, seed(s) type, relative maturity (RM) of planted seed(s), seed population), (e) fertilizer data (for example, nutrient type (Nitrogen, Phosphorous, Potassium), application type, application date, amount, source, method), (f) chemical application data (for example, pesticide, herbicide, fungicide, other substance or mixture of substances intended for use as a plant regulator, defoliant, or desiccant, application date, amount, source, method), (g) irrigation data (for example, application date, amount, source, method), (h) weather data (for example, precipitation, rainfall rate, predicted rainfall, water runoff rate region, temperature, wind, forecast, pressure, visibility, clouds, heat index, dew point, humidity, snow depth, air quality, sunrise, sunset), (i) imagery data (for example, imagery and light spectrum information from an agricultural apparatus sensor, camera, computer, smartphone, tablet, unmanned aerial vehicle, planes or satellite), (j) scouting observations (photos, videos, free form notes, voice recordings, voice transcriptions, weather conditions (temperature, precipitation (current and over time), soil moisture, crop growth stage, wind velocity, relative humidity, dew point, black layer)), and (k) soil, seed, crop phenology, pest and disease reporting, and predictions sources and databases.

A data server computer 108 is communicatively coupled to agricultural intelligence computer system 130 and is programmed or configured to send external data 110 to agricultural intelligence computer system 130 via the network(s) 109. The external data server computer 108 may be owned or operated by the same legal person or entity as the agricultural intelligence computer system 130, or by a different person or entity such as a government agency, non-governmental organization (NGO), and/or a private data service provider. Examples of external data include weather data, imagery data, soil data, or statistical data relating to crop yields, among others. External data 110 may consist of the same type of information as field data 106. In some embodiments, the external data 110 is provided by an external data server 108 owned by the same entity that owns and/or operates the agricultural intelligence computer system 130. For example, the agricultural intelligence computer system 130 may include a data server focused exclusively on a type of data that might otherwise be obtained from third party sources, such as weather data. In some embodiments, an external data server 108 may actually be incorporated within the system 130.

An agricultural apparatus 111 may have one or more remote sensors 112 fixed thereon, which sensors are communicatively coupled either directly or indirectly via agricultural apparatus 111 to the agricultural intelligence computer system 130 and are programmed or configured to send sensor data to agricultural intelligence computer system 130. Examples of agricultural apparatus 111 include tractors, combines, harvesters, planters, trucks, fertilizer equipment, aerial vehicles including unmanned aerial vehicles, and any other item of physical machinery or hardware, typically mobile machinery, and which may be used in tasks associated with agriculture. In some embodiments, a single unit of apparatus 111 may comprise a plurality of sensors 112 that are coupled locally in a network on the apparatus; controller area network (CAN) is example of such a network that can be installed in combines, harvesters, sprayers, and cultivators. Application controller 114 is communicatively coupled to agricultural intelligence computer system 130 via the network(s) 109 and is programmed or configured to receive one or more scripts that are used to control an operating parameter of an agricultural vehicle or implement from the agricultural intelligence computer system 130. For instance, a controller area network (CAN) bus interface may be used to enable communications from the agricultural intelligence computer system 130 to the agricultural apparatus 111, such as how the CLIMATE FIELDVIEW DRIVE, available from The Climate Corporation, San Francisco, California, is used. Sensor data may consist of the same type of information as field data 106. In some embodiments, remote sensors 112 may not be fixed to an agricultural apparatus 111 but may be remotely located in the field and may communicate with network 109.

The apparatus 111 may comprise a cab computer 115 that is programmed with a cab application, which may comprise a version or variant of the mobile application for device 104 that is further described in other sections herein. In an embodiment, cab computer 115 comprises a compact computer, often a tablet-sized computer or smartphone, with a graphical screen display, such as a color display, that is mounted within an operator's cab of the apparatus 111. Cab computer 115 may implement some or all of the operations and functions that are described further herein for the mobile computer device 104.

The network(s) 109 broadly represent any combination of one or more data communication networks including local area networks, wide area networks, internetworks or internets, using any of wireline or wireless links, including terrestrial or satellite links. The network(s) may be implemented by any medium or mechanism that provides for the exchange of data between the various elements of FIG. 1. The various elements of FIG. 1 may also have direct (wired or wireless) communications links. The sensors 112, controller 114, external data server computer 108, and other elements of the system each comprise an interface compatible with the network(s) 109 and are programmed or configured to use standardized protocols for communication across the networks such as TCP/IP, Bluetooth, CAN protocol and higher-layer protocols such as HTTP, TLS, and the like.

Agricultural intelligence computer system 130 is programmed or configured to receive field data 106 from field manager computing device 104, external data 110 from external data server computer 108, and sensor data from remote sensor 112. Agricultural intelligence computer system 130 may be further configured to host, use or execute one or more computer programs, other software elements, digitally programmed logic such as FPGAs or ASICs, or any combination thereof to perform translation and storage of data values, construction of digital models of one or more crops on one or more fields, generation of recommendations and notifications, and generation and sending of scripts to application controller 114, in the manner described further in other sections of this disclosure.

In an embodiment, agricultural intelligence computer system 130 is programmed with or comprises a communication layer 132, presentation layer 134, data management layer 140, hardware/virtualization layer 150, and model and field data repository 160. "Layer," in this context, refers to any combination of electronic digital interface circuits, microcontrollers, firmware such as drivers, and/or computer programs or other software elements.

Communication layer 132 may be programmed or configured to perform input/output interfacing functions including sending requests to field manager computing device 104, external data server computer 108, and remote sensor 112 for field data, external data, and sensor data respectively. Communication layer 132 may be programmed or configured to send the received data to model and field data repository 160 to be stored as field data 106.

Presentation layer 134 may be programmed or configured to generate a graphical user interface (GUI) to be displayed on field manager computing device 104, cab computer 115 or other computers that are coupled to the system 130 through the network 109. The GUI may comprise controls for inputting data to be sent to agricultural intelligence computer system 130, generating requests for models and/or recommendations, and/or displaying recommendations, notifications, models, and other field data.

Data management layer 140 may be programmed or configured to manage read operations and write operations involving the repository 160 and other functional elements of the system, including queries and result sets communicated between the functional elements of the system and the repository. Examples of data management layer 140 include JDBC, SQL server interface code, and/or HADOOP interface code, among others. Repository 160 may comprise a database. As used herein, the term "database" may refer to either a body of data, a relational database management system (RDBMS), or to both. As used herein, a database may comprise any collection of data including hierarchical databases, relational databases, flat file databases, object-relational databases, object oriented databases, distributed databases, and any other structured collection of records or data that is stored in a computer system. Examples of RDBMS's include, but are not limited to including, ORACLE®, MYSQL, IBM® DB2, MICROSOFT® SQL SERVER, SYBASE®, and POSTGRESQL databases. However, any database may be used that enables the systems and methods described herein.

When field data 106 is not provided directly to the agricultural intelligence computer system via one or more agricultural machines or agricultural machine devices that interacts with the agricultural intelligence computer system, the user may be prompted via one or more user interfaces on the user device (served by the agricultural intelligence computer system) to input such information. In an example embodiment, the user may specify identification data by accessing a map on the user device (served by the agricultural intelligence computer system) and selecting specific CLUs that have been graphically shown on the map. In an alternative embodiment, the user 102 may specify identification data by accessing a map on the user device (served by the agricultural intelligence computer system 130) and drawing boundaries of the field over the map. Such CLU selection or map drawings represent geographic identifiers. In alternative embodiments, the user may specify identification data by accessing field identification data (provided as shape files or in a similar format) from the U.S. Department of Agriculture Farm Service Agency or other source via the user device and providing such field identification data to the agricultural intelligence computer system.

In an example embodiment, the agricultural intelligence computer system 130 is programmed to generate and cause displaying a graphical user interface comprising a data manager for data input. After one or more fields have been identified using the methods described above, the data manager may provide one or more graphical user interface widgets which when selected can identify changes to the field, soil, crops, tillage, or nutrient practices. The data manager may include a timeline view, a spreadsheet view, and/or one or more editable programs.

Figure 5:
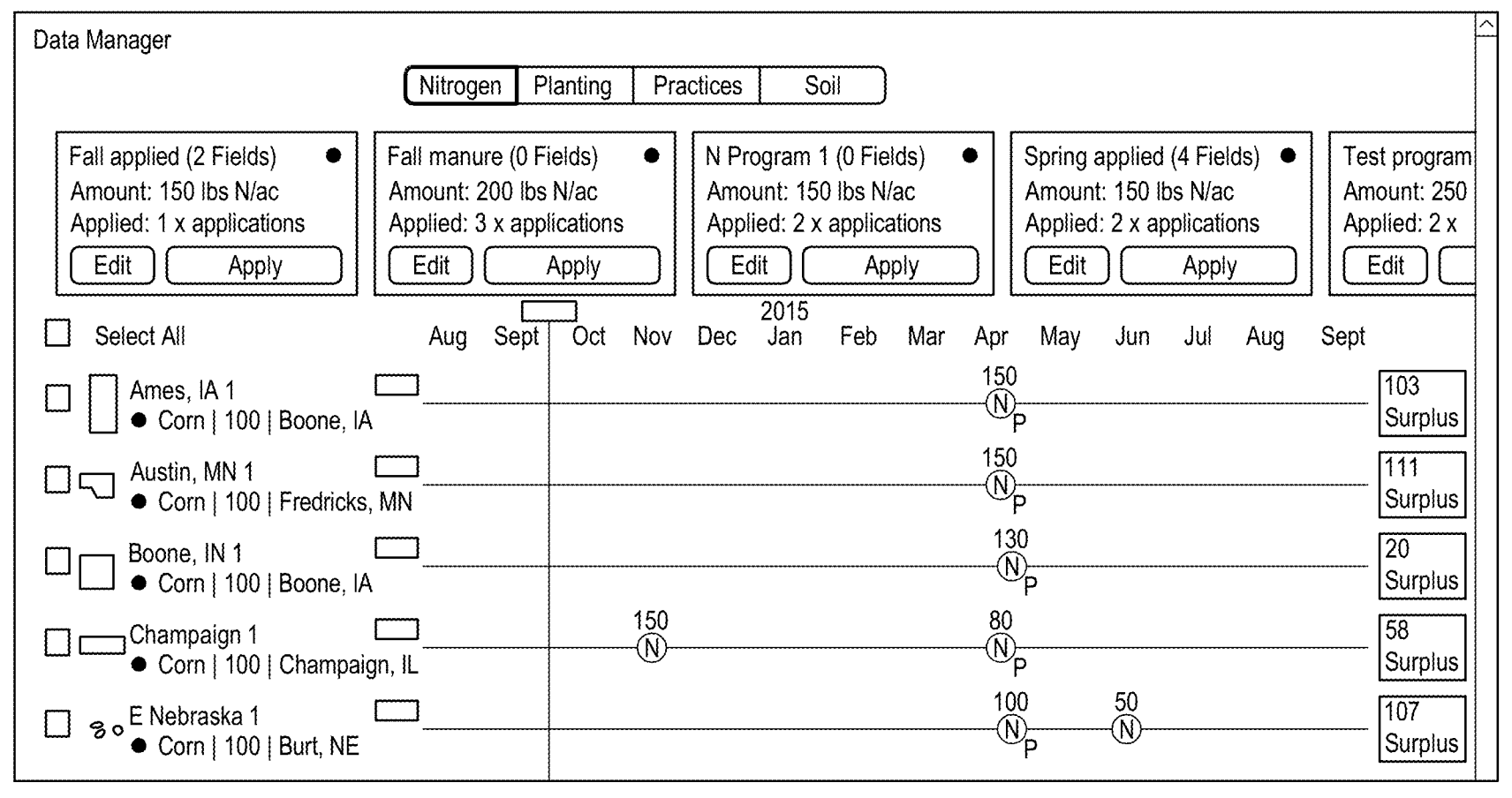

FIG. 5 depicts an example embodiment of a timeline view for data entry. Using the display depicted in FIG. 5, a user computer can input a selection of a particular field and a particular date for the addition of event. Events depicted at the top of the timeline may include Nitrogen, Planting, Practices, and Soil. To add a nitrogen application event, a user computer may provide input to select the nitrogen tab. The user computer may then select a location on the timeline for a particular field in order to indicate an application of nitrogen on the selected field. In response to receiving a selection of a location on the timeline for a particular field, the data manager may display a data entry overlay, allowing the user computer to input data pertaining to nitrogen applications, planting procedures, soil application, tillage procedures, irrigation practices, or other information relating to the particular field. For example, if a user computer selects a portion of the timeline and indicates an application of nitrogen, then the data entry overlay may include fields for inputting an amount of nitrogen applied, a date of application, a type of fertilizer used, and any other information related to the application of nitrogen.

In an embodiment, the data manager provides an interface for creating one or more programs. "Program," in this context, refers to a set of data pertaining to nitrogen applications, planting procedures, soil application, tillage procedures, irrigation practices, or other information that may be related to one or more fields, and that can be stored in digital data storage for reuse as a set in other operations. After a program has been created, it may be conceptually applied to one or more fields and references to the program may be stored in digital storage in association with data identifying the fields. Thus, instead of manually entering identical data relating to the same nitrogen applications for multiple different fields, a user computer may create a program that indicates a particular application of nitrogen and then apply the program to multiple different fields. For example, in the timeline view of FIG. 5, the top two timelines have the "Spring applied" program selected, which includes an application of 150 lbs N/ac in early April. The data manager may provide an interface for editing a program. In an embodiment, when a particular program is edited, each field that has selected the particular program is edited. For example, in FIG. 5, if the "Spring applied" program is edited to reduce the application of nitrogen to 130 lbs N/ac, the top two fields may be updated with a reduced application of nitrogen based on the edited program.

In an embodiment, in response to receiving edits to a field that has a program selected, the data manager removes the correspondence of the field to the selected program. For example, if a nitrogen application is added to the top field in FIG. 5, the interface may update to indicate that the "Spring applied" program is no longer being applied to the top field. While the nitrogen application in early April may remain, updates to the "Spring applied" program would not alter the April application of nitrogen.

FIG. 6 depicts an example embodiment of a spreadsheet view for data entry. Using the display depicted in FIG. 6, a user can create and edit information for one or more fields. The data manager may include spreadsheets for inputting information with respect to Nitrogen, Planting, Practices, and Soil as depicted in FIG. 6. To edit a particular entry, a user computer may select the particular entry in the spreadsheet and update the values. For example, FIG. 6 depicts an in-progress update to a target yield value for the second field. Additionally, a user computer may select one or more fields in order to apply one or more programs. In response to receiving a selection of a program for a particular field, the data manager may automatically complete the entries for the particular field based on the selected program. As with the timeline view, the data manager may update the entries for each field associated with a particular program in response to receiving an update to the program. Additionally, the data manager may remove the correspondence of the selected program to the field in response to receiving an edit to one of the entries for the field.

In an embodiment, model and field data is stored in model and field data repository 160. Model data comprises data models created for one or more fields. For example, a crop model may include a digitally constructed model of the development of a crop on the one or more fields. "Model," in this context, refers to an electronic digitally stored set of executable instructions and data values, associated with one another, which are capable of receiving and responding to a programmatic or other digital call, invocation, or request for resolution based upon specified input values, to yield one or more stored or calculated output values that can serve as the basis of computer-implemented recommendations, output data displays, or machine control, among other things. Persons of skill in the field find it convenient to express models using mathematical equations, but that form of expression does not confine the models disclosed herein to abstract concepts; instead, each model herein has a practical application in a computer in the form of stored executable instructions and data that implement the model using the computer. The model may include a model of past events on the one or more fields, a model of the current status of the one or more fields, and/or a model of predicted events on the one or more fields. Model and field data may be stored in data structures in memory, rows in a database table, in flat files or spreadsheets, or other forms of stored digital data.

In an embodiment, agricultural intelligence computer system 130 is programmed to comprise a classification model management server computer (server) 170. The server 170 is further configured to comprise model configuration instructions 172, model construction instructions 174, model execution instructions 176, and user interface instructions 178.

In some embodiments, the model configuration instructions 172 offer computer-executable instructions to collect initial image data and determine values of certain parameters of a digital model for recognizing plant diseases from the initial image data. When the digital model is the SSD, the initial image data may be plant photos that include marked regions each labeled with an identifier of a plant disease. The marked regions can be further processed with respect to the full images in building a training set for the SSD. The initial image data can also be simply the marked regions with corresponding labels. The relevant parameters of the SSD include a group of anchor boxes. The model configuration instructions 172 offer computer-executable instructions to specifically build anchor boxes that represent symptoms of plant diseases.

In some embodiments, the model construction instructions 174 offer computer-executable instructions to construct the training set and train the digital model with the training set. The training set can include images of a certain size having the marked regions and corresponding labels or cropped, padded, or scaled versions of the images having equivalent marked regions and and corresponding labels. When the digital model is the SSD, the training set also includes mappings of the marked regions to the anchor boxes.

In some embodiments, the model execution instructions 176 offer computer-executable instructions to apply the digital model to new images for classification. The new image can be a new plant photo showing symptoms of one or more plant diseases in one or more regions. The new image may need to be similarly cropped, padded, or scaled before being fed into the digital model. When the digital model is the SSD, application of the digital model is expected to produce at least one classification into a certain plant disease for each of the one or more regions.

In some embodiments, the user interface instructions 178 offer computer-executable instructions to manage communications with other devices. The communications may include receiving the initial image data including the labels from an image source, receiving a new photo for classification from a client device, sending classification results for the new photo to the client device, or sending digital data representing the SSD to another client device.

Each component of the server 170 comprises a set of one or more pages of main memory, such as RAM, in the agricultural intelligence computer system 130 into which executable instructions have been loaded and which when executed cause the agricultural intelligence computing system to perform the functions or operations that are described herein with reference to those modules. For example, the model configuration module 172 may comprise a set of pages in RAM that contain instructions which when executed cause performing the location selection functions that are described herein. The instructions may be in machine executable code in the instruction set of a CPU and may have been compiled based upon source code written in JAVA, C, C++, OBJECTIVE-C, or any other human-readable programming language or environment, alone or in combination with scripts in JAVASCRIPT, other scripting languages and other programming source text. The term "pages" is intended to refer broadly to any region within main memory and the specific terminology used in a system may vary depending on the memory architecture or processor architecture. In another embodiment, each component of the server 170 also may represent one or more files or projects of source code that are digitally stored in a mass storage device such as non-volatile RAM or disk storage, in the agricultural intelligence computer system 130 or a separate repository system, which when compiled or interpreted cause generating executable instructions which when executed cause the agricultural intelligence computing system to perform the functions or operations that are described herein with reference to those modules. In other words, the drawing figure may represent the manner in which programmers or software developers organize and arrange source code for later compilation into an executable, or interpretation into bytecode or the equivalent, for execution by the agricultural intelligence computer system 130.

Figure 4:
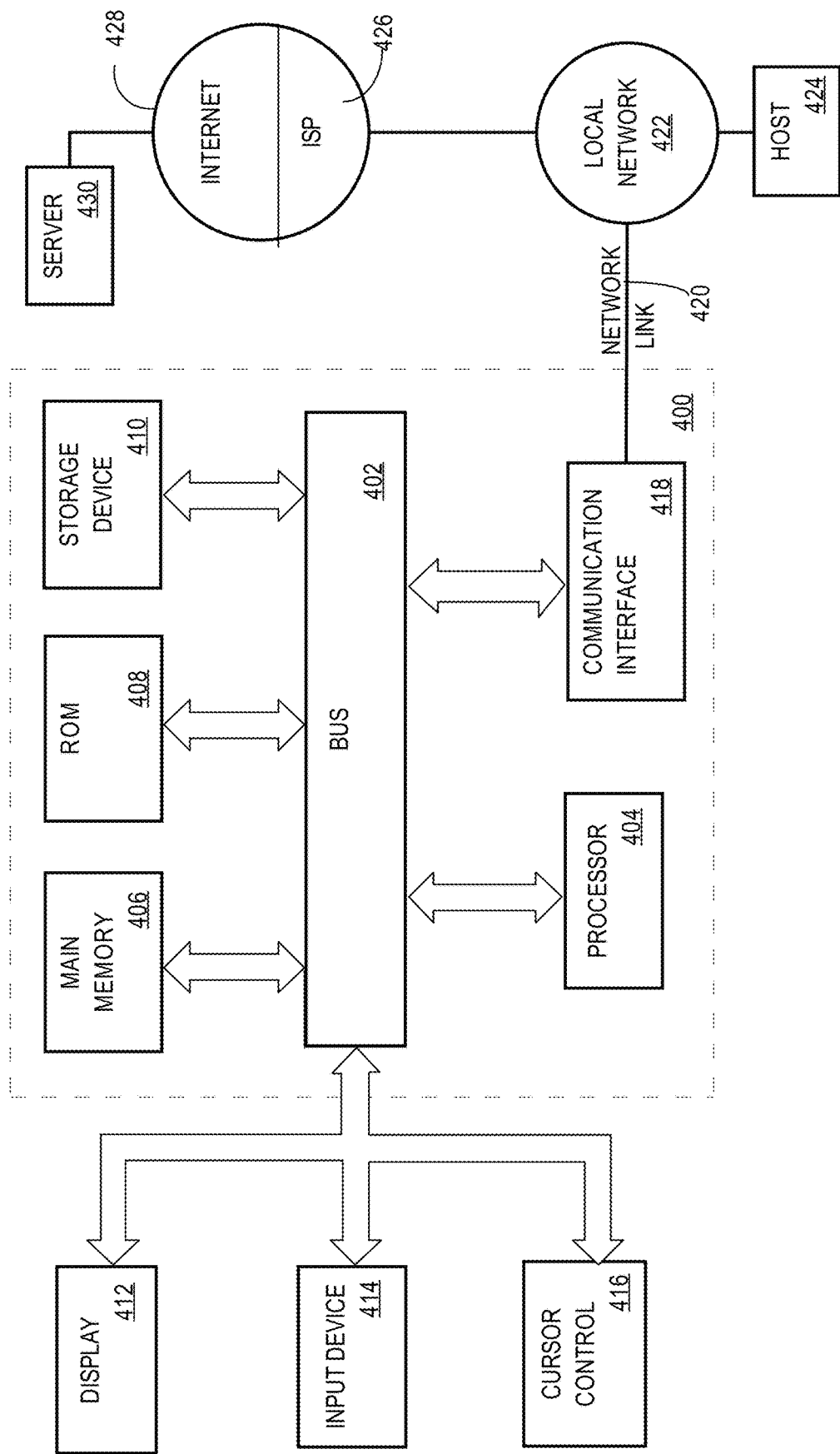
FIG. 4 is a block diagram that illustrates a computer system upon which an embodiment of the invention may be implemented.

Hardware/virtualization layer 150 comprises one or more central processing units (CPUs), memory controllers, and other devices, components, or elements of a computer system such as volatile or non-volatile memory, non-volatile storage such as disk, and I/O devices or interfaces as illustrated and described, for example, in connection with FIG. 4. The layer 150 also may comprise programmed instructions that are configured to support virtualization, containerization, or other technologies.

For purposes of illustrating a clear example, FIG. 1 shows a limited number of instances of certain functional elements. However, in other embodiments, there may be any number of such elements. For example, embodiments may use thousands or millions of different mobile computing devices 104 associated with different users. Further, the system 130 and/or external data server computer 108 may be implemented using two or more processors, cores, clusters, or instances of physical machines or virtual machines, configured in a discrete location or co-located with other elements in a datacenter, shared computing facility or cloud computing facility.

2.2. Application Program Overview

In an embodiment, the implementation of the functions described herein using one or more computer programs or other software elements that are loaded into and executed using one or more general-purpose computers will cause the general-purpose computers to be configured as a particular machine or as a computer that is specially adapted to perform the functions described herein. Further, each of the flow diagrams that are described further herein may serve, alone or in combination with the descriptions of processes and functions in prose herein, as algorithms, plans or directions that may be used to program a computer or logic to implement the functions that are described. In other words, all the prose text herein, and all the drawing figures, together are intended to provide disclosure of algorithms, plans or directions that are sufficient to permit a skilled person to program a computer to perform the functions that are described herein, in combination with the skill and knowledge of such a person given the level of skill that is appropriate for inventions and disclosures of this type.

In an embodiment, user 102 interacts with agricultural intelligence computer system 130 using field manager computing device 104 configured with an operating system and one or more application programs or apps; the field manager computing device 104 also may interoperate with the agricultural intelligence computer system independently and automatically under program control or logical control and direct user interaction is not always required. Field manager computing device 104 broadly represents one or more of a smart phone, PDA, tablet computing device, laptop computer, desktop computer, workstation, or any other computing device capable of transmitting and receiving information and performing the functions described herein. Field manager computing device 104 may communicate via a network using a mobile application stored on field manager computing device 104, and in some embodiments, the device may be coupled using a cable 113 or connector to the sensor 112 and/or controller 114. A particular user 102 may own, operate or possess and use, in connection with system 130, more than one field manager computing device 104 at a time.

The mobile application may provide client-side functionality, via the network to one or more mobile computing devices. In an example embodiment, field manager computing device 104 may access the mobile application via a web browser or a local client application or app. Field manager computing device 104 may transmit data to, and receive data from, one or more front-end servers, using web-based protocols or formats such as HTTP, XML, and/or JSON, or app-specific protocols. In an example embodiment, the data may take the form of requests and user information input, such as field data, into the mobile computing device. In some embodiments, the mobile application interacts with location tracking hardware and software on field manager computing device 104 which determines the location of field manager computing device 104 using standard tracking techniques such as multilateration of radio signals, the global positioning system (GPS), WiFi positioning systems, or other methods of mobile positioning. In some cases, location data or other data associated with the device 104, user 102, and/or user account(s) may be obtained by queries to an operating system of the device or by requesting an app on the device to obtain data from the operating system.

In an embodiment, field manager computing device 104 sends field data 106 to agricultural intelligence computer system 130 comprising or including, but not limited to, data values representing one or more of: a geographical location of the one or more fields, tillage information for the one or more fields, crops planted in the one or more fields, and soil data extracted from the one or more fields. Field manager computing device 104 may send field data 106 in response to user input from user 102 specifying the data values for the one or more fields. Additionally, field manager computing device 104 may automatically send field data 106 when one or more of the data values becomes available to field manager computing device 104. For example, field manager computing device 104 may be communicatively coupled to remote sensor 112 and/or application controller 114 which include an irrigation sensor and/or irrigation controller. In response to receiving data indicating that application controller 114 released water onto the one or more fields, field manager computing device 104 may send field data 106 to agricultural intelligence computer system 130 indicating that water was released on the one or more fields. Field data 106 identified in this disclosure may be input and communicated using electronic digital data that is communicated between computing devices using parameterized URLs over HTTP, or another suitable communication or messaging protocol.

A commercial example of the mobile application is CLIMATE FIELDVIEW, commercially available from The Climate Corporation, San Francisco, California. The CLIMATE FIELDVIEW application, or other applications, may be modified, extended, or adapted to include features, functions, and programming that have not been disclosed earlier than the filing date of this disclosure. In one embodiment, the mobile application comprises an integrated software platform that allows a grower to make fact-based decisions for their operation because it combines historical data about the grower's fields with any other data that the grower wishes to compare. The combinations and comparisons may be performed in real time and are based upon scientific models that provide potential scenarios to permit the grower to make better, more informed decisions.

FIG. 2 illustrates two views of an example logical organization of sets of instructions in main memory when an example mobile application is loaded for execution. In FIG. 2, each named element represents a region of one or more pages of RAM or other main memory, or one or more blocks of disk storage or other non-volatile storage, and the programmed instructions within those regions. In one embodiment, in view (a), a mobile computer application 200 comprises account-fields-data ingestion-sharing instructions 202, overview and alert instructions 204, digital map book instructions 206, seeds and planting instructions 208, nitrogen instructions 210, weather instructions 212, field health instructions 214, and performance instructions 216.

In one embodiment, a mobile computer application 200 comprises account, fields, data ingestion, sharing instructions 202 which are programmed to receive, translate, and ingest field data from third party systems via manual upload or APIs. Data types may include field boundaries, yield maps, as-planted maps, soil test results, as-applied maps, and/or management zones, among others. Data formats may include shape files, native data formats of third parties, and/or farm management information system (FMIS) exports, among others. Receiving data may occur via manual upload, e-mail with attachment, external APIs that push data to the mobile application, or instructions that call APIs of external systems to pull data into the mobile application. In one embodiment, mobile computer application 200 comprises a data inbox. In response to receiving a selection of the data inbox, the mobile computer application 200 may display a graphical user interface for manually uploading data files and importing uploaded files to a data manager.

In one embodiment, digital map book instructions 206 comprise field map data layers stored in device memory and are programmed with data visualization tools and geospatial field notes. This provides growers with convenient information close at hand for reference, logging and visual insights into field performance. In one embodiment, overview and alert instructions 204 are programmed to provide an operation-wide view of what is important to the grower, and timely recommendations to take action or focus on particular issues. This permits the grower to focus time on what needs attention, to save time and preserve yield throughout the season. In one embodiment, seeds and planting instructions 208 are programmed to provide tools for seed selection, hybrid placement, and script creation, including variable rate (VR) script creation, based upon scientific models and empirical data. This enables growers to maximize yield or return on investment through optimized seed purchase, placement and population.

In one embodiment, script generation instructions 205 are programmed to provide an interface for generating scripts, including variable rate (VR) fertility scripts. The interface enables growers to create scripts for field implements, such as nutrient applications, planting, and irrigation. For example, a planting script interface may comprise tools for identifying a type of seed for planting. Upon receiving a selection of the seed type, mobile computer application 200 may display one or more fields broken into management zones, such as the field map data layers created as part of digital map book instructions 206. In one embodiment, the management zones comprise soil zones along with a panel identifying each soil zone and a soil name, texture, drainage for each zone, or other field data. Mobile computer application 200 may also display tools for editing or creating such, such as graphical tools for drawing management zones, such as soil zones, over a map of one or more fields. Planting procedures may be applied to all management zones or different planting procedures may be applied to different subsets of management zones. When a script is created, mobile computer application 200 may make the script available for download in a format readable by an application controller, such as an archived or compressed format. Additionally, and/or alternatively, a script may be sent directly to cab computer 115 from mobile computer application 200 and/or uploaded to one or more data servers and stored for further use.

In one embodiment, nitrogen instructions 210 are programmed to provide tools to inform nitrogen decisions by visualizing the availability of nitrogen to crops. This enables growers to maximize yield or return on investment through optimized nitrogen application during the season. Example programmed functions include displaying images such as SSURGO images to enable drawing of fertilizer application zones and/or images generated from subfield soil data, such as data obtained from sensors, at a high spatial resolution (as fine as millimeters or smaller depending on sensor proximity and resolution); upload of existing grower-defined zones; providing a graph of plant nutrient availability and/or a map to enable tuning application(s) of nitrogen across multiple zones; output of scripts to drive machinery; tools for mass data entry and adjustment; and/or maps for data visualization, among others. "Mass data entry," in this context, may mean entering data once and then applying the same data to multiple fields and/or zones that have been defined in the system; example data may include nitrogen application data that is the same for many fields and/or zones of the same grower, but such mass data entry applies to the entry of any type of field data into the mobile computer application 200. For example, nitrogen instructions 210 may be programmed to accept definitions of nitrogen application and practices programs and to accept user input specifying to apply those programs across multiple fields. "Nitrogen application programs," in this context, refers to stored, named sets of data that associates: a name, color code or other identifier, one or more dates of application, types of material or product for each of the dates and amounts, method of application or incorporation such as injected or broadcast, and/or amounts or rates of application for each of the dates, crop or hybrid that is the subject of the application, among others. "Nitrogen practices programs," in this context, refer to stored, named sets of data that associates: a practices name; a previous crop; a tillage system; a date of primarily tillage; one or more previous tillage systems that were used; one or more indicators of application type, such as manure, that were used. Nitrogen instructions 210 also may be programmed to generate and cause displaying a nitrogen graph, which indicates projections of plant use of the specified nitrogen and whether a surplus or shortfall is predicted; in some embodiments, different color indicators may signal a magnitude of surplus or magnitude of shortfall. In one embodiment, a nitrogen graph comprises a graphical display in a computer display device comprising a plurality of rows, each row associated with and identifying a field; data specifying what crop is planted in the field, the field size, the field location, and a graphic representation of the field perimeter; in each row, a timeline by month with graphic indicators specifying each nitrogen application and amount at points correlated to month names; and numeric and/or colored indicators of surplus or shortfall, in which color indicates magnitude.

In one embodiment, the nitrogen graph may include one or more user input features, such as dials or slider bars, to dynamically change the nitrogen planting and practices programs so that a user may optimize his nitrogen graph. The user may then use his optimized nitrogen graph and the related nitrogen planting and practices programs to implement one or more scripts, including variable rate (VR) fertility scripts. Nitrogen instructions 210 also may be programmed to generate and cause displaying a nitrogen map, which indicates projections of plant use of the specified nitrogen and whether a surplus or shortfall is predicted; in some embodiments, different color indicators may signal a magnitude of surplus or magnitude of shortfall. The nitrogen map may display projections of plant use of the specified nitrogen and whether a surplus or shortfall is predicted for different times in the past and the future (such as daily, weekly, monthly or yearly) using numeric and/or colored indicators of surplus or shortfall, in which color indicates magnitude. In one embodiment, the nitrogen map may include one or more user input features, such as dials or slider bars, to dynamically change the nitrogen planting and practices programs so that a user may optimize his nitrogen map, such as to obtain a preferred amount of surplus to shortfall. The user may then use his optimized nitrogen map and the related nitrogen planting and practices programs to implement one or more scripts, including variable rate (VR) fertility scripts. In other embodiments, similar instructions to the nitrogen instructions 210 could be used for application of other nutrients (such as phosphorus and potassium), application of pesticide, and irrigation programs.

In one embodiment, weather instructions 212 are programmed to provide field-specific recent weather data and forecasted weather information. This enables growers to save time and have an efficient integrated display with respect to daily operational decisions.

In one embodiment, field health instructions 214 are programmed to provide timely remote sensing images highlighting in-season crop variation and potential concerns. Example programmed functions include cloud checking, to identify possible clouds or cloud shadows; determining nitrogen indices based on field images; graphical visualization of scouting layers, including, for example, those related to field health, and viewing and/or sharing of scouting notes; and/or downloading satellite images from multiple sources and prioritizing the images for the grower, among others.

In one embodiment, performance instructions 216 are programmed to provide reports, analysis, and insight tools using on-farm data for evaluation, insights and decisions. This enables the grower to seek improved outcomes for the next year through fact-based conclusions about why return on investment was at prior levels, and insight into yield-limiting factors. The performance instructions 216 may be programmed to communicate via the network(s) 109 to back-end analytics programs executed at agricultural intelligence computer system 130 and/or external data server computer 108 and configured to analyze metrics such as yield, yield differential, hybrid, population, SSURGO zone, soil test properties, or elevation, among others. Programmed reports and analysis may include yield variability analysis, treatment effect estimation, benchmarking of yield and other metrics against other growers based on anonymized data collected from many growers, or data for seeds and planting, among others.

Applications having instructions configured in this way may be implemented for different computing device platforms while retaining the same general user interface appearance. For example, the mobile application may be programmed for execution on tablets, smartphones, or server computers that are accessed using browsers at client computers. Further, the mobile application as configured for tablet computers or smartphones may provide a full app experience or a cab app experience that is suitable for the display and processing capabilities of cab computer 115. For example, referring now to view (b) of FIG. 2, in one embodiment a cab computer application 220 may comprise maps-cab instructions 222, remote view instructions 224, data collect and transfer instructions 226, machine alerts instructions 228, script transfer instructions 230, and scouting-cab instructions 232. The code base for the instructions of view (b) may be the same as for view (a) and executables implementing the code may be programmed to detect the type of platform on which they are executing and to expose, through a graphical user interface, only those functions that are appropriate to a cab platform or full platform. This approach enables the system to recognize the distinctly different user experience that is appropriate for an in-cab environment and the different technology environment of the cab. The maps-cab instructions 222 may be programmed to provide map views of fields, farms or regions that are useful in directing machine operation. The remote view instructions 224 may be programmed to turn on, manage, and provide views of machine activity in real-time or near real-time to other computing devices connected to the system 130 via wireless networks, wired connectors or adapters, and the like. The data collect and transfer instructions 226 may be programmed to turn on, manage, and provide transfer of data collected at sensors and controllers to the system 130 via wireless networks, wired connectors or adapters, and the like. The machine alerts instructions 228 may be programmed to detect issues with operations of the machine or tools that are associated with the cab and generate operator alerts. The script transfer instructions 230 may be configured to transfer in scripts of instructions that are configured to direct machine operations or the collection of data. The scouting-cab instructions 232 may be programmed to display location-based alerts and information received from the system 130 based on the location of the field manager computing device 104, agricultural apparatus 111, or sensors 112 in the field and ingest, manage, and provide transfer of location-based scouting observations to the system 130 based on the location of the agricultural apparatus 111 or sensors 112 in the field.

2.3. Data Ingest to the Computer System

In an embodiment, external data server computer 108 stores external data 110, including soil data representing soil composition for the one or more fields and weather data representing temperature and precipitation on the one or more fields. The weather data may include past and present weather data as well as forecasts for future weather data. In an embodiment, external data server computer 108 comprises a plurality of servers hosted by different entities. For example, a first server may contain soil composition data while a second server may include weather data. Additionally, soil composition data may be stored in multiple servers. For example, one server may store data representing percentage of sand, silt, and clay in the soil while a second server may store data representing percentage of organic matter (OM) in the soil.

In an embodiment, remote sensor 112 comprises one or more sensors that are programmed or configured to produce one or more observations. Remote sensor 112 may be aerial sensors, such as satellites, vehicle sensors, planting equipment sensors, tillage sensors, fertilizer or insecticide application sensors, harvester sensors, and any other implement capable of receiving data from the one or more fields. In an embodiment, application controller 114 is programmed or configured to receive instructions from agricultural intelligence computer system 130. Application controller 114 may also be programmed or configured to control an operating parameter of an agricultural vehicle or implement. For example, an application controller may be programmed or configured to control an operating parameter of a vehicle, such as a tractor, planting equipment, tillage equipment, fertilizer or insecticide equipment, harvester equipment, or other farm implements such as a water valve. Other embodiments may use any combination of sensors and controllers, of which the following are merely selected examples.

The system 130 may obtain or ingest data under user 102 control, on a mass basis from a large number of growers who have contributed data to a shared database system. This form of obtaining data may be termed "manual data ingest" as one or more user-controlled computer operations are requested or triggered to obtain data for use by the system 130. As an example, the CLIMATE FIELDVIEW application, commercially available from The Climate Corporation, San Francisco, California, may be operated to export data to system 130 for storing in the repository 160.

For example, seed monitor systems can both control planter apparatus components and obtain planting data, including signals from seed sensors via a signal harness that comprises a CAN backbone and point-to-point connections for registration and/or diagnostics. Seed monitor systems can be programmed or configured to display seed spacing, population and other information to the user via the cab computer 115 or other devices within the system 130. Examples are disclosed in U.S. Pat. No. 8,738,243 and US Pat. Pub. 20150094916, and the present disclosure assumes knowledge of those other patent disclosures.

Likewise, yield monitor systems may contain yield sensors for harvester apparatus that send yield measurement data to the cab computer 115 or other devices within the system 130. Yield monitor systems may utilize one or more remote sensors 112 to obtain grain moisture measurements in a combine or other harvester and transmit these measurements to the user via the cab computer 115 or other devices within the system 130.

In an embodiment, examples of sensors 112 that may be used with any moving vehicle or apparatus of the type described elsewhere herein include kinematic sensors and position sensors. Kinematic sensors may comprise any of speed sensors such as radar or wheel speed sensors, accelerometers, or gyros. Position sensors may comprise GPS receivers or transceivers, or WiFi-based position or mapping apps that are programmed to determine location based upon nearby WiFi hotspots, among others.

In an embodiment, examples of sensors 112 that may be used with tractors or other moving vehicles include engine speed sensors, fuel consumption sensors, area counters or distance counters that interact with GPS or radar signals, PTO (power take-off) speed sensors, tractor hydraulics sensors configured to detect hydraulics parameters such as pressure or flow, and/or and hydraulic pump speed, wheel speed sensors or wheel slippage sensors. In an embodiment, examples of controllers 114 that may be used with tractors include hydraulic directional controllers, pressure controllers, and/or flow controllers; hydraulic pump speed controllers; speed controllers or governors; hitch position controllers; or wheel position controllers provide automatic steering.

In an embodiment, examples of sensors 112 that may be used with seed planting equipment such as planters, drills, or air seeders include seed sensors, which may be optical, electromagnetic, or impact sensors; downforce sensors such as load pins, load cells, pressure sensors; soil property sensors such as reflectivity sensors, moisture sensors, electrical conductivity sensors, optical residue sensors, or temperature sensors; component operating criteria sensors such as planting depth sensors, downforce cylinder pressure sensors, seed disc speed sensors, seed drive motor encoders, seed conveyor system speed sensors, or vacuum level sensors; or pesticide application sensors such as optical or other electromagnetic sensors, or impact sensors. In an embodiment, examples of controllers 114 that may be used with such seed planting equipment include: toolbar fold controllers, such as controllers for valves associated with hydraulic cylinders; downforce controllers, such as controllers for valves associated with pneumatic cylinders, airbags, or hydraulic cylinders, and programmed for applying downforce to individual row units or an entire planter frame; planting depth controllers, such as linear actuators; metering controllers, such as electric seed meter drive motors, hydraulic seed meter drive motors, or swath control clutches; hybrid selection controllers, such as seed meter drive motors, or other actuators programmed for selectively allowing or preventing seed or an air-seed mixture from delivering seed to or from seed meters or central bulk hoppers; metering controllers, such as electric seed meter drive motors, or hydraulic seed meter drive motors; seed conveyor system controllers, such as controllers for a belt seed delivery conveyor motor; marker controllers, such as a controller for a pneumatic or hydraulic actuator; or pesticide application rate controllers, such as metering drive controllers, orifice size or position controllers.

In an embodiment, examples of sensors 112 that may be used with tillage equipment include position sensors for tools such as shanks or discs; tool position sensors for such tools that are configured to detect depth, gang angle, or lateral spacing; downforce sensors; or draft force sensors. In an embodiment, examples of controllers 114 that may be used with tillage equipment include downforce controllers or tool position controllers, such as controllers configured to control tool depth, gang angle, or lateral spacing.

In an embodiment, examples of sensors 112 that may be used in relation to apparatus for applying fertilizer, insecticide, fungicide and the like, such as on-planter starter fertilizer systems, subsoil fertilizer applicators, or fertilizer sprayers, include: fluid system criteria sensors, such as flow sensors or pressure sensors; sensors indicating which spray head valves or fluid line valves are open; sensors associated with tanks, such as fill level sensors; sectional or system-wide supply line sensors, or row-specific supply line sensors; or kinematic sensors such as accelerometers disposed on sprayer booms. In an embodiment, examples of controllers 114 that may be used with such apparatus include pump speed controllers; valve controllers that are programmed to control pressure, flow, direction, PWM and the like; or position actuators, such as for boom height, subsoiler depth, or boom position.

In an embodiment, examples of sensors 112 that may be used with harvesters include yield monitors, such as impact plate strain gauges or position sensors, capacitive flow sensors, load sensors, weight sensors, or torque sensors associated with elevators or augers, or optical or other electromagnetic grain height sensors; grain moisture sensors, such as capacitive sensors; grain loss sensors, including impact, optical, or capacitive sensors; header operating criteria sensors such as header height, header type, deck plate gap, feeder speed, and reel speed sensors; separator operating criteria sensors, such as concave clearance, rotor speed, shoe clearance, or chaffer clearance sensors; auger sensors for position, operation, or speed; or engine speed sensors. In an embodiment, examples of controllers 114 that may be used with harvesters include header operating criteria controllers for elements such as header height, header type, deck plate gap, feeder speed, or reel speed; separator operating criteria controllers for features such as concave clearance, rotor speed, shoe clearance, or chaffer clearance; or controllers for auger position, operation, or speed.

In an embodiment, examples of sensors 112 that may be used with grain carts include weight sensors, or sensors for auger position, operation, or speed. In an embodiment, examples of controllers 114 that may be used with grain carts include controllers for auger position, operation, or speed.

In an embodiment, examples of sensors 112 and controllers 114 may be installed in unmanned aerial vehicle (UAV) apparatus or "drones." Such sensors may include cameras with detectors effective for any range of the electromagnetic spectrum including visible light, infrared, ultraviolet, near-infrared (NIR), and the like; accelerometers; altimeters; temperature sensors; humidity sensors; pitot tube sensors or other airspeed or wind velocity sensors; battery life sensors; or radar emitters and reflected radar energy detection apparatus; other electromagnetic radiation emitters and reflected electromagnetic radiation detection apparatus. Such controllers may include guidance or motor control apparatus, control surface controllers, camera controllers, or controllers programmed to turn on, operate, obtain data from, manage and configure any of the foregoing sensors. Examples are disclosed in U.S. patent application Ser. No. 14/831,165 and the present disclosure assumes knowledge of that other patent disclosure.

In an embodiment, sensors 112 and controllers 114 may be affixed to soil sampling and measurement apparatus that is configured or programmed to sample soil and perform soil chemistry tests, soil moisture tests, and other tests pertaining to soil. For example, the apparatus disclosed in U.S. patent application Ser. No. 15/551,582, filed on Aug. 16, 2017, may be used, and the present disclosure assumes knowledge of those patent disclosures.

In an embodiment, sensors 112 and controllers 114 may comprise weather devices for monitoring weather conditions of fields. For example, the apparatus disclosed in U.S. Provisional Application No. 62/154,207, filed on Apr. 29, 2015, U.S. Provisional Application No. 62/175,160, filed on Jun. 12, 2015, U.S. Provisional Application No. 62/198,060, filed on Jul. 28, 2015, and U.S. Provisional Application No. 62/220,852, filed on Sep. 18, 2015, may be used, and the present disclosure assumes knowledge of those patent disclosures.

2.4. Process Overview—Agronomic Model Training

In an embodiment, the agricultural intelligence computer system 130 is programmed or configured to create an agronomic model. In this context, an agronomic model is a data structure in memory of the agricultural intelligence computer system 130 that comprises field data 106, such as identification data and harvest data for one or more fields. The agronomic model may also comprise calculated agronomic properties which describe either conditions which may affect the growth of one or more crops on a field, or properties of the one or more crops, or both. Additionally, an agronomic model may comprise recommendations based on agronomic factors such as crop recommendations, irrigation recommendations, planting recommendations, fertilizer recommendations, fungicide recommendations, pesticide recommendations, harvesting recommendations and other crop management recommendations. The agronomic factors may also be used to estimate one or more crop related results, such as agronomic yield. The agronomic yield of a crop is an estimate of quantity of the crop that is produced, or in some examples the revenue or profit obtained from the produced crop.

In an embodiment, the agricultural intelligence computer system 130 may use a preconfigured agronomic model to calculate agronomic properties related to currently received location and crop information for one or more fields. The preconfigured agronomic model is based upon previously processed field data, including but not limited to, identification data, harvest data, fertilizer data, and weather data. The preconfigured agronomic model may have been cross validated to ensure accuracy of the model. Cross validation may include comparison to ground truthing that compares predicted results with actual results on a field, such as a comparison of precipitation estimate with a rain gauge or sensor providing weather data at the same or nearby location or an estimate of nitrogen content with a soil sample measurement.

Figure 3:
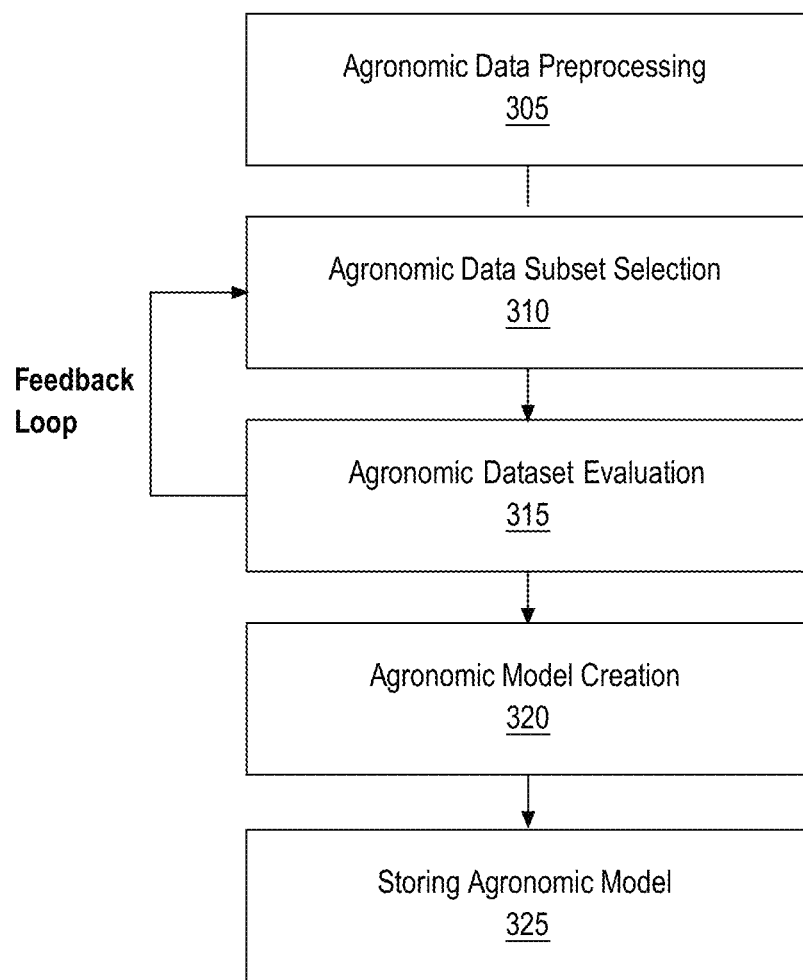
FIG. 3 illustrates a programmed process by which the agricultural intelligence computer system generates one or more preconfigured agronomic models using agronomic data provided by one or more data sources.

FIG. 3 illustrates a programmed process by which the agricultural intelligence computer system generates one or more preconfigured agronomic models using field data provided by one or more data sources. FIG. 3 may serve as an algorithm or instructions for programming the functional elements of the agricultural intelligence computer system 130 to perform the operations that are now described.

At block 305, the agricultural intelligence computer system 130 is configured or programmed to implement agronomic data preprocessing of field data received from one or more data sources. The field data received from one or more data sources may be preprocessed for the purpose of removing noise, distorting effects, and confounding factors within the agronomic data including measured outliers that could adversely affect received field data values. Embodiments of agronomic data preprocessing may include, but are not limited to, removing data values commonly associated with outlier data values, specific measured data points that are known to unnecessarily skew other data values, data smoothing, aggregation, or sampling techniques used to remove or reduce additive or multiplicative effects from noise, and other filtering or data derivation techniques used to provide clear distinctions between positive and negative data inputs.

At block 310, the agricultural intelligence computer system 130 is configured or programmed to perform data subset selection using the preprocessed field data in order to identify datasets useful for initial agronomic model generation. The agricultural intelligence computer system 130 may implement data subset selection techniques including, but not limited to, a genetic algorithm method, an all subset models method, a sequential search method, a stepwise regression method, a particle swarm optimization method, and an ant colony optimization method. For example, a genetic algorithm selection technique uses an adaptive heuristic search algorithm, based on evolutionary principles of natural selection and genetics, to determine and evaluate datasets within the preprocessed agronomic data.

At block 315, the agricultural intelligence computer system 130 is configured or programmed to implement field dataset evaluation. In an embodiment, a specific field dataset is evaluated by creating an agronomic model and using specific quality thresholds for the created agronomic model. Agronomic models may be compared and/or validated using one or more comparison techniques, such as, but not limited to, root mean square error with leave-one-out cross validation (RMSECV), mean absolute error, and mean percentage error. For example, RMSECV can cross validate agronomic models by comparing predicted agronomic property values created by the agronomic model against historical agronomic property values collected and analyzed. In an embodiment, the agronomic dataset evaluation logic is used as a feedback loop where agronomic datasets that do not meet configured quality thresholds are used during future data subset selection steps (block 310).

At block 320, the agricultural intelligence computer system 130 is configured or programmed to implement agronomic model creation based upon the cross validated agronomic datasets. In an embodiment, agronomic model creation may implement multivariate regression techniques to create preconfigured agronomic data models.

At block 325, the agricultural intelligence computer system 130 is configured or programmed to store the preconfigured agronomic data models for future field data evaluation.

2.5. Implementation Example—Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

For example, FIG. 4 is a block diagram that illustrates a computer system 400 upon which an embodiment of the invention may be implemented. Computer system 400 includes a bus 402 or other communication mechanism for communicating information, and a hardware processor 404 coupled with bus 402 for processing information. Hardware processor 404 may be, for example, a general purpose microprocessor.

Computer system 400 also includes a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Such instructions, when stored in non-transitory storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk, optical disk, or solid-state drive is provided and coupled to bus 402 for storing information and instructions.

Computer system 400 may be coupled via bus 402 to a display 412, such as a cathode ray tube (CRT), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane.

Computer system 400 may implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor 404 executing one or more sequences of one or more instructions contained in main memory 406. Such instructions may be read into main memory 406 from another storage medium, such as storage device 410. Execution of the sequences of instructions contained in main memory 406 causes processor 404 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 410. Volatile media includes dynamic memory, such as main memory 406. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 402. Transmission media can also take the form of acoustic or light waves, such as those generated during radio-wave and infrared data communications.

Various forms of media may be involved in carrying one or more sequences of one or more instructions to processor 404 for execution. For example, the instructions may initially be carried on a magnetic disk or solid-state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infrared signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

3. Functional Descriptions

3.1 Plant Disease Detection

Today, a variety of classification methods based on image analysis are available. These classification methods can be used to analyze photos of plants and classify the photos into given disease classes or a healthy class, thereby detecting potential infection of the plants by the corresponding diseases. Some of these classification methods involve CNNs, including the SSD.

Generally, an SSD starts with a base CNN comprising a series of convolutional layers that correspond to receptive fields of different scales. The SSD then performs classification using feature maps produced by not only the last convolutional layer but also the other convolutional layers. More specifically, the SSD utilizes a set of user-defined anchor boxes, which typically have different sizes and aspect ratios that correspond to various features of given classes, for each of those convolutional layers in the base CNN. The SSD then incorporates a set of 4+c small (e.g., 3×3) filters for each of the anchor boxes (in a so-called convolutional feature layer), with 4 corresponding to four sides of an anchor box and c being the number of classes, for each of the convolutional layers. These small filters are trained with ground truth images of known features for each of the classes. These ground truth images can have various sizes and aspect ratios, and each image is associated with a class and an anchor box. These small filters can then be used to determine whether an area delineated by one of the anchor boxes in a feature map produced by the corresponding convolutional layer matches features of one of the classes.

As described above, the SSD can recognize various features of the classes having various scales and aspect ratios in one or more images and classify portions of the images into the classes with associated confidence scores accordingly in a single shot without requiring an initial, separate round of region proposal to locate the features in the images. It is possible that the SSD initially classifies a region of an image into multiple classes. Non-maximum suppression (NMS) can be applied to select one of the multiple classes as the final classification. The SSD has been shown to be faster than previous single shot detectors and also more accurate, in fact as accurate as slower techniques that perform explicit region proposals and pooling. Third-party libraries that implement SSD-related functions using the Keras library and Python are available on the GitHub platform, which may use the VGG16 as the base CNN, for example.

3.2 Digital Model Configuration

In some embodiments, the server 170 is programmed to construct a digital model for detecting infection of plant diseases from plant photos using the SSD. For corn, the common plant diseases include Anthracnose Leaf Blight (ALB), Common Rust (CR), Eyespot (EYE), Gray Leaf Spot (GLS), Goss's Wilt (GW), Northern Leaf Blight (NLB), Northern Leaf Spot (NLS), Southern Leaf Blight (SLB), and Southern Rust (SR). The digital model can be designed to classify images into a certain number of classes corresponding to a certain number of such plant diseases. The server 170 is programmed to first receive a set of images, such as photos of corn leaves, which can have marked regions of disease symptoms or directly feature such disease symptoms.

FIG. 7A includes example photos of corn leaves each having symptoms of one disease. The image 720 shows symptoms of GLS within the box (defining a marked region) 704 and within the box 706. The box 704 labeled with "GLS" includes one lesion, while the box 706 also labeled with "GLS" includes disconnected but closely-located lesions, which is not uncommon. The box 704 and the box 706 have different sizes and similar but distinct aspect ratios. Having a single box 706 instead of multiple boxes for each of the disconnected lesions may increase efficiency in training and executing the digital model. The image 722 shows symptoms of SR within the box 708, which includes a large cluster of separate lesions as is often the case. The box 708 also has a distinct size and aspect ratio.

Figure 7B:
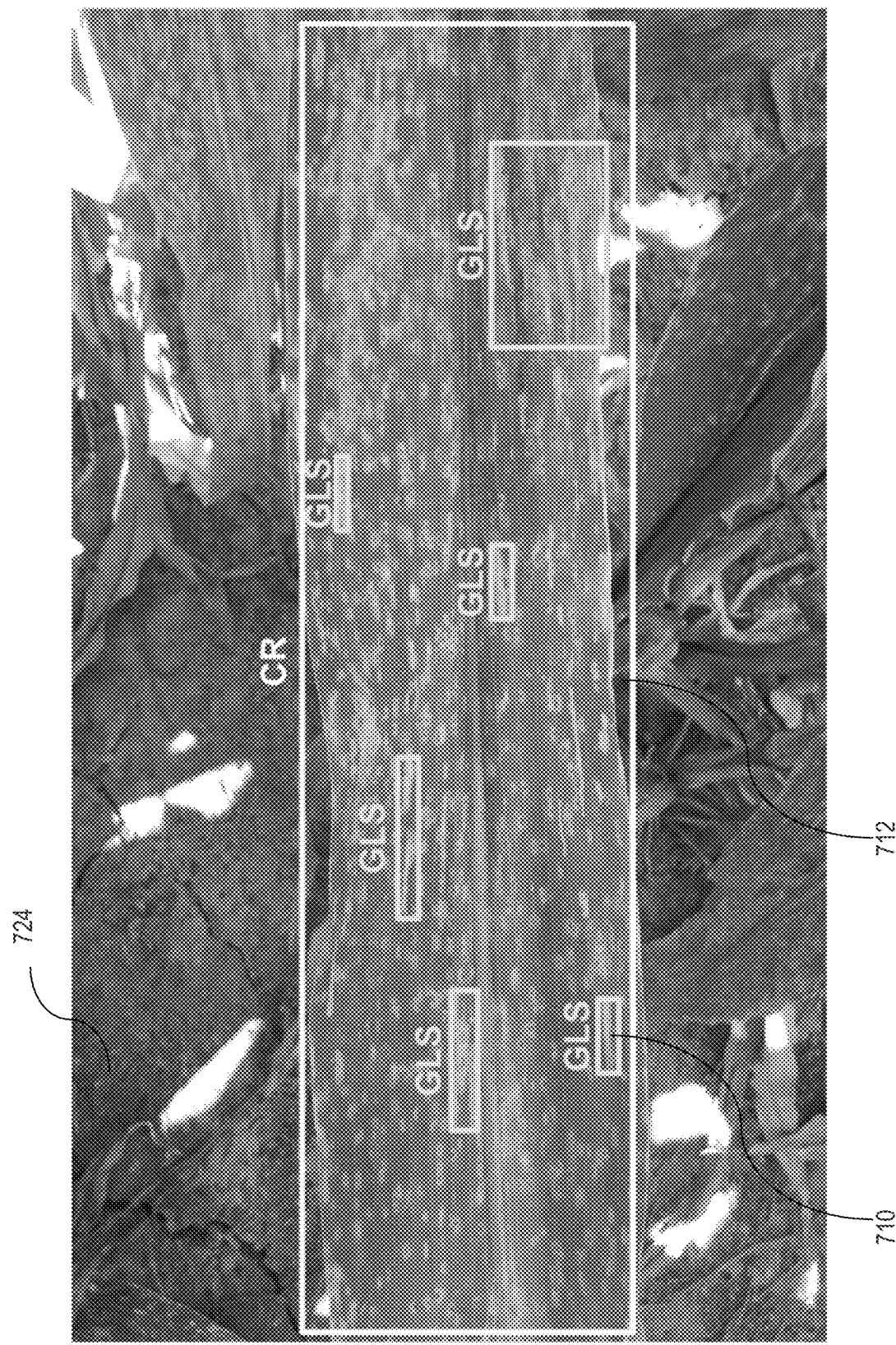
FIG. 7B includes an example photo of a corn leaf having symptoms of multiple diseases.

FIG. 7B includes an example photo of a corn leaf having symptoms of multiple diseases. The image 724 shows symptoms of GLS within the box 710. The image 724 also shows symptoms of CR within the box 712, which includes many separate lesions. The box 710 labeled with "GLS" and the box 712 labeled with "CR" each have a distinct size and aspect ratio. While the box 712 includes lesions of multiple diseases, as the lesions from CR dominate, this marked region corresponding to the box 712 may still serve as a good sample for CR.

In some embodiments, the server 170 is programmed to process each image having marked regions subject to certain rules, which can complete or enhance the marking. The server 170 can be configured to break each marked region into multiple ones or combine multiple marked regions into one in accordance with a restriction on a size of a marked region, a density of a cluster of lesions, or a size proportion between a cluster and a leaf. For example, instead of marking the box 712, the image 724 might have had just a small marked region for an individual CR lesion. The server 170 can be programmed to automatically extend that marked region to the box 712 from detecting nearby lesions and determining the total size of the cluster of lesions relative to the size of the leaf. In addition, the server 170 can be configured to limit the number of marked regions in each image, such as no more than six, to simplify the SSD training process. For example, the server 170 can be programmed to automatically reduce the number of marked regions in the image 724 from the current seven to six by deselecting the marked region having the smallest size or one having a similar aspect ratio as another marked region.

In some embodiments, the server 170 is programmed to define anchor boxes for the convolutional layers in the SSD. Each anchor box can be defined in terms of a unit length, an aspect ratio, and a scaling factor. For example, the unit length can be ten pixels, the aspect ratio of width to height can be 1.0, and a scaling factor can be 1, leading to an anchor box of ten pixels in width and ten pixels in length. The aspect ratio can be 2.0 instead, leading to an anchor box of twenty pixels in width and ten pixels in length. The scaling factor can be 2.0 instead, leading to an anchor box of twenty pixels in width and twenty pixels in length. The server 170 can be programmed to use the marked regions, such as those corresponding to the boxes 704, 706, 708, 710, or 712, to guide the definition of anchor boxes. The server 170 can be programmed to normalize the marked regions (e.g., to a fixed distance between the camera and the plant and a fixed camera resolution), group similarly-sized ones into one cluster, and compute an aggregate size and aspect ratio for each cluster to determine the scaling factors and aspect ratios. As the series of convolutional layers in a base CNN typically correspond to increasingly larger receptive fields, the server can be programmed to assign increasingly larger scaling factors to the series of convolutional layers. The server can also be programmed to utilize a scaling factor, such as 0.1, that is smaller than the scaling factors used in a typical implementation of the SSD to help identify very small lesions produced by certain corn diseases or other very small disease symptoms. For example, the scaling factors can be [0.1, 0.2, 0.37, 0.54, 0.71, 0.88, 1.05] for a series of six convolutional layers, with one scaling factor for all anchor boxes assigned to one convolutional layer. For corn diseases, the common aspect ratios include 1.0/7.0, 1.0/5.0, 1.0/3.0, 0.5, 1.0, 2.0, 3.0, 5.0, or 7.0.

3.3 Training Set and Digital Model Construction

In some embodiments, the server 170 is programmed to scale, pad, or otherwise process the images to produce final images for the training set. For example, the max_crop_and_resize and random_pad_and_resize functions available on the GitHub platform can be adapted to generate variants of the original images. The server 170 is programmed to associate each variant with the marked regions and corresponding labels as in the original image. For plant disease detection, the classes correspond to plant diseases, and each label identifies one of the plant diseases. The images do not need to be rotated to produce additional images for the training set when symmetric aspect ratios are used for the anchor boxes. To detect infection of corn diseases, the number of marked regions can be at least 100 for each of the corn diseases.

In some embodiments, the server 170 is programmed to match the training set of images to the anchor boxes, as required for building an SSD. For example, the SSDBox-Encoder available on the GitHub platform can be adapted to also refer to the variants of the original images for such matching purposes, with pos_iou_threshold set to 0.5 and neg_iou_threshold set to 0.2. The server 170 is programmed to then build the digital model for recognizing corn diseases from the bounding boxes and the training set, including images with the marked regions or their variants, the associated class labels, and the associated matches to the anchor boxes. For example, the model.fit_generator function in the Keras library can be used with lr_schedule set to 0.001.

3.4 Digital Model Execution

In some embodiments, the server 170 is programmed to receive a new image, such as a photo of a corn plant, and apply the digital model to the new image. The server 170 is programmed to convert the new image into a square image as necessary. Instead of cropping the new image causing information loss, the server 170 can be configured to provide padding to create an updated image where each edge is as long as the long edge of the new image. The server 170 can be configured to further center the new image in the updated image and scale the result to obtain a final input image.

In some embodiments, the server 170 is programmed to then execute the digital model on the final input image. For example, the decode_y function available on the GitHub platform can be used to implement the execution, with confidence_thresh set to 0.8 and iou_threshold set to 0.5 for NMS.

FIG. 8 illustrates an example process of applying NMS to refine an initial classification result to a final classification result. The image 802 is a photo of part of a corn leaf. As discussed above, the SSD may initially classify a region of an image into multiple classes. In this example, each of the boxes, including the box 804 and the box 808, delineates an area of the image that has been classified into one of the classes corresponding to corn diseases. In particular, the box 808 is among a set of boxes that cover the pixel 806 or the surrounding region. Before application of the NMS, those boxes where the associated confidence scores are lower than a certain threshold, such as confidence_thresh, can be filtered out. In this example, the classification of box 804 is associated with a low confidence and thus can be removed. Through the NMS, the box with the largest score is then selected, all the other boxes that overlap with that box for more than a particular threshold, such as iou_threshold, are then removed, and the process continues until no more box can be removed. In this example, the box 808 is the only box left, and thus the pixel 806 will is classified based on the box 808.

3.5 Example Processes

FIG. 9 illustrates an example method performed by a server computer that is programmed for configuring and utilizing a CNN for plant disease detection. FIG. 9 is intended to disclose an algorithm, plan or outline that can be used to implement one or more computer programs or other software elements which when executed cause performing the functional improvements and technical advances that are described herein. Furthermore, the flow diagrams herein are described at the same level of detail that persons of ordinary skill in the art ordinarily use to communicate with one another about algorithms, plans, or specifications forming a basis of software programs that they plan to code or implement using their accumulated skill and knowledge.

In some embodiments, in step 902, the server 170 is programmed or configured to receive a set of photos of plants infected with a plurality of diseases. Specifically, the set of photos show leaves with a plurality of marked regions having multiple aspect ratios. Each marked region is associated with a label of one of the plurality of diseases and showing at least one lesion caused by the one disease. The set of photos includes a specific photo showing a specific leaf having a specific marked region that shows multiple lesions. For any such specific photo, a total size of the multiple lesions would be greater than a first predefined percentage of a size of the specific marked region. In addition, the size of the specific marked region would be greater than a second predefined percentage of a size of the specific leaf. For example, the set of photos would show infected corn leaves, one of the photos would show a leaf having a cluster of lesions for one of the corn diseases, where the lesions are positioned close to one another and occupy a majority of the leaf.

In some embodiments, in step 904, the server 170 is programmed or configured to determine a group of anchor boxes from the plurality of marked regions for each of a series of convolutional layers of an SSD. Each of the group of anchor boxes generally has a distinct aspect ratio representative of at least a subset of the plurality of marked regions that can correspond to similar symptoms of one disease. For corn, the aspect ratio can be as large as 7:1. The series of convolutional layers tend to have increasingly bigger receptive fields, therefore the server 170 can be programmed to assign bigger anchor boxes to later convolutional layers.

In some embodiments, in step 906, after determining the group of anchor boxes, the server 170 can be programmed to further map each of the plurality of marked regions to one of the group of anchor boxes. The server can be configured to match a marked region with an anchor box when a size percentage of an intersection over an union of the marked region and the anchor box over the union is greater than a specific threshold.

In some embodiments, in step 908, the server 170 is programmed or configured to build the SSD from the group of anchor boxes, the set of photos with the plurality of marked regions, the associated plurality of labels of diseases, and the associated plurality of mappings to anchor boxes. For training purposes, the set of original photos can be augmented with variants obtained from cropping, padding, resizing, or performing another image processing operation on the original photos. The variants are associated with equivalent marked regions and corresponding labels as in the original photos. Even through these image processing operations, the aspect ratios of the marked regions are to be preserved and associated with the same mappings to the anchor boxes as in the original photos.

In some embodiments, in step 910, the server 170 is programmed or configured to receive a new image from a client device. The new image can be a photo of a plant that shows symptoms of one or more diseases in one or more regions. In step 912, the server 170 is programmed or configured to apply the SSD to the new image to identify those symptoms of the one or more diseases in the one or more regions of the new image.

In some embodiments, in step 914, the server 170 is programmed or configured to transmit data related to the one or more diseases or one or more regions to the client device. The data can identify each of the one or more regions and one or more classifications of the region. The data can also include a confidence score for each of the one or more classifications into one of the plant diseases.

4. Extensions and Alternatives

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A system for configuring and utilizing deep learning for plant disease recognition, the system comprising:
   a memory; and
   a processor coupled to the memory and configured to perform:
      receiving a set of photos of plants showing leaves with a plurality of marked regions having multiple aspect ratios, each marked region being associated with a label of a disease of a plurality of diseases and showing at least one lesion caused by the disease;
      dividing, combining, or removing one or more of the plurality of marked regions to create a new set of marked regions in accordance with a restriction on a size of a marked region, on a size proportion of a cluster of lesions within a marked region to a leaf, or on a density of lesions within a marked region based on a predefined percentage;
      normalizing one or more of the marked regions in the new set of marked regions based on a fixed distance between a camera and a plant and a fixed camera resolution;
      determining, by the processor, a group of anchor boxes from the new set of marked regions for each of a series of convolutional layers of a single shot multibox detector (SSD), the SSD configured to receive an image and assign each of one or more areas of the image into at least one of a plurality of classes corresponding to the plurality of diseases, the group of anchor boxes having distinct aspect ratios and corresponding to various features of the plurality of classes;
      mapping each of the plurality of marked regions to one of the groups of anchor boxes;
      building the SSD from the group of anchor boxes, the set of photos having the plurality of marked regions, the associated plurality of labels, and the associated plurality of mappings;
      receiving a new image from a client device; and
      applying the SSD to the new image to identify symptoms of one or more diseases in one or more areas of the new image.

2. The system of claim 1, wherein the SSD comprises the series of convolutional layers that correspond to receptive fields of different scales; and
   wherein the processor is further configured to perform:
      performing classification using feature maps produced by each of the series of convolutional layers.

3. The system of claim 1, wherein the SSD comprises 4+c filters for each of the group of anchor boxes, with c being a size of the plurality of classes corresponding to the plurality of diseases.

4. The system of claim 1, wherein the SSD includes a fixed number of filters of a fixed size, for each of the group of anchor boxes, to be applied to feature maps produced by each of the series of convolutional layers.

5. The system of claim 1, wherein one of the plurality of marked regions shows multiple disconnected lesions having different sizes or aspect ratios.

6. The system of claim 1, wherein the processor is further configured to perform adding additional photos to the set of photos by cropping and resizing a copy of a first photo of the set of photos or by randomly padding and resizing a copy of a second photo of the set of photos.

7. The system of claim 1, wherein the processor is configured, in connection with performing the mapping, to perform matching a marked region with one of the group of anchor boxes when a size percentage of an intersection over an union of the marked region and the anchor box over the union is greater than a specific threshold.

8. The system of claim 1, wherein the processor is configured, in connection with performing the mapping, to perform matching a marked region with a negative anchor box outside the group of anchor boxes when a size percentage of an intersection over an union of the marked region and the anchor box over the union is less than a specific threshold.

9. The system of claim 1, wherein the processor is configured, in connection with performing the determining, to perform deselecting a first marked region from the plurality of marked regions that has a smallest size or a size similar to a second marked region of the plurality of marked regions.

10. The system of claim 1, wherein the processor is configured, in connection with performing the determining, to perform:
    clustering the plurality of marked regions into multiple clusters;
    computing an aggregate region for a cluster of the multiple clusters; and
    defining an anchor box of the group of anchor boxes based on the cluster.

11. The system of claim 1, wherein the processor is configured, in connection with performing the determining, to perform:
    identifying each of the group of anchor boxes by a unit length, an aspect ratio, and a scaling factor; and
    assigning a smaller scaling factor to the group of anchor boxes for a convolutional layer earlier in the series of convolutional layers and assigning a larger scaling factor to the group of anchor boxes for a convolutional layer later in the series of convolutional layers.

12. The system of claim 11, wherein the plants are corn plants, and wherein the aspect ratio is 1.0/7.0, 1.0/5.0, 1.0/3.0, 0.5, 1.0, 2.0, 3.0, 5.0, or 7.0.

13. The system of claim 1, wherein the processor is configured, in connection with performing the applying, to perform assigning the one or more areas of the new image into one or more classes of the plurality of classes corresponding to the one or more of the plurality of diseases.

14. A system for configuring and utilizing deep learning for plant disease recognition, the system comprising:
    a memory; and
    a processor coupled to the memory and configured to perform:

receiving a set of photos of plants showing leaves with a plurality of marked regions having multiple aspect ratios, each marked region being associated with a label of a disease of a plurality of diseases and showing at least one lesion caused by the disease;

normalizing one or more of the plurality of marked regions based on a fixed distance between a camera and a plant and a fixed camera resolution;

determining, by the processor, a group of anchor boxes from the plurality of marked regions for each of a series of convolutional layers of a single shot multibox detector (SSD), the SSD configured to receive an image and assign each of one or more areas of the image into at least one of a plurality of classes corresponding to the plurality of diseases, the group of anchor boxes having distinct aspect ratios and corresponding to various features of the plurality of classes;

mapping each of the plurality of marked regions to one of the groups of anchor boxes;

building the SSD from the group of anchor boxes, the set of photos having the plurality of marked regions, the associated plurality of labels, and the associated plurality of mappings;

receiving a new image from a client device; and applying the SSD to the new image to identify symptoms of one or more of the plurality of diseases in one or more areas of the new image.

15. A computer-implemented method of configuring and utilizing deep learning for plant disease recognition, the method comprising:

receiving, by a processor, a set of photos of plants showing leaves with a plurality of marked regions having multiple aspect ratios, each marked region being associated with a label of a disease of a plurality of diseases and showing at least one lesion caused by the disease;

normalizing, by the processor, one or more of the plurality of marked regions based on a fixed distance between a camera and a plant and a fixed camera resolution;

determining, by the processor, a group of anchor boxes from the plurality of marked regions for each of a series of convolutional layers of a single shot multibox detector (SSD), the SSD configured to receive an image and assign each of one or more areas of the image into at least one of a plurality of classes corresponding to the plurality of diseases, the group of anchor boxes having distinct aspect ratios and corresponding to various features of the plurality of classes;

mapping each of the plurality of marked regions to one of the groups of anchor boxes, comprising: matching a marked region with an anchor box when a superimposition of the anchor box covers more than a predefined percentage of the marked region and matching a marked region with a negative anchor box outside the group of anchor boxes in response to a size percentage of an intersection over a union of the marked region and the anchor box over the union being less than a specific threshold;

building the SSD from the group of anchor boxes, the set of photos having the plurality of marked regions, the associated plurality of labels, and the associated plurality of mappings;

receiving a new image from a client device; and applying the SSD to the new image to identify symptoms of one or more diseases in one or more areas of the new image.

16. The computer-implemented method of claim 15, wherein one of the plurality of marked regions shows multiple disconnected lesions having different sizes or aspect ratios.

* * * * *